United States Patent
Ohnishi et al.

(10) Patent No.: US 6,410,613 B1
(45) Date of Patent: *Jun. 25, 2002

(54) PHOSPHATE COMPOUND AND PREPARATION PROCESS THEREOF, PHOSPHATE COPPER COMPOUND AND PREPARATION PROCESS THEREOF, NEAR INFRARED RAY ABSORBER, AND NEAR INFRARED RAY-ABSORBING ACRYLIC RESIN COMPOSITION

(75) Inventors: Yasuhiro Ohnishi, Kyoto; Hiroki Katono, Fukushima, both of (JP)

(73) Assignee: Kureha Kagaku Kogyo Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/485,882

(22) PCT Filed: Aug. 25, 1998

(86) PCT No.: PCT/JP98/03757

§ 371 (c)(1),
(2), (4) Date: Feb. 17, 2000

(87) PCT Pub. No.: WO99/10354

PCT Pub. Date: Mar. 4, 1999

(30) Foreign Application Priority Data

Aug. 26, 1997 (JP) .............................................. 9-229723
Aug. 26, 1997 (JP) .............................................. 9-229727
Aug. 26, 1997 (JP) .............................................. 9-229731

(51) Int. Cl.$^7$ ................................................ G21F 1/10
(52) U.S. Cl. ........................ 523/136; 252/587; 524/145
(58) Field of Search ................................ 524/413, 145; 252/587; 556/24; 558/183, 186, 97, 92, 208, 114; 523/136; 47/9, 26, 28.1

(56) References Cited

U.S. PATENT DOCUMENTS

| | | | | |
|---|---|---|---|---|
| 3,227,673 A | * | 1/1966 | Duke et al. ................. | 558/114 |
| 3,331,896 A | * | 7/1967 | Eiseman et al. ............. | 558/92 |
| 3,462,520 A | | 8/1969 | Nehmsmann et al. | |
| 3,467,683 A | * | 9/1969 | Harson et al. ............... | 556/24 |
| 3,678,086 A | * | 7/1972 | Lynch et al. ................. | 556/24 |
| 3,988,275 A | * | 10/1976 | Satake et al. ............... | 524/145 |
| 4,587,063 A | * | 5/1986 | Kurosaki et al. ........... | 558/114 |
| 4,939,285 A | * | 7/1990 | Weis et al. .................. | 558/131 |
| 5,256,718 A | * | 10/1993 | Yamomoto et al. ......... | 524/412 |
| 5,611,965 A | * | 3/1997 | Shoujii et al. ............... | 252/587 |
| 5,800,861 A | * | 9/1998 | Chiang et al. ............... | 523/135 |
| 5,872,272 A | * | 2/1999 | Yano et al. ................... | 556/24 |
| 5,961,893 A | * | 10/1999 | Honda et al. ................ | 252/587 |

FOREIGN PATENT DOCUMENTS

| | | |
|---|---|---|
| GB | 1121683 | 7/1968 |
| JP | 41-14416 B1 | 8/1966 |
| JP | 50-64226 A | 5/1975 |
| JP | 55-142045 A | 11/1980 |
| JP | 55-142068 A | 11/1980 |
| JP | 59-48493 A | 3/1984 |
| JP | 63-159386 A | 7/1988 |
| JP | 63-254671 A | 10/1988 |
| JP | 2-264788 A | 10/1990 |
| JP | 5-170748 A | 7/1993 |
| JP | 9-211220 A | 8/1997 |

* cited by examiner

Primary Examiner—Veronica P. Hoke
(74) Attorney, Agent, or Firm—Frishauf, Holtz, Goodman, Langer & Chick, P.C.

(57) ABSTRACT

Disclosed herein are a novel phosphate compound by which a copper ion can be dispersed in a high proportion in a synthetic resin, thereby providing excellent visible ray-transmitting property and performance that near infrared rays are absorbed with high efficiency, a preparation process thereof, a phosphate copper compound obtained from the phosphate compound and a preparation process thereof, and a near infrared ray-absorbing acrylic resin composition which has both excellent visible ray-transmitting property and near infrared rays absorption capability.

12 Claims, 10 Drawing Sheets

PHOSPHATE COMPOUND AND PREPARATION PROCESS THEREOF, PHOSPHATE COPPER COMPOUND AND PREPARATION PROCESS THEREOF, NEAR INFRARED RAY ABSORBER, AND NEAR INFRARED RAY-ABSORBING ACRYLIC RESIN COMPOSITION

TECHNICAL FIELD

The present invention relates to novel phosphate compounds and a preparation process thereof, novel phosphate copper compounds and a preparation process thereof, near infrared ray absorbers containing a copper ion, and near infrared ray-absorbing acrylic resin compositions having excellent visible ray-transmitting property and performance that near infrared rays are absorbed with high efficiency.

BACKGROUND ART

A great number of attempts have heretofore been made to impart performance that near infrared rays are absorbed with high efficiency to synthetic resins. For example, resin compositions in which an organic pigment having near infrared ray-absorbing ability is contained in an acrylic resin have been known (see Japanese Patent Application Laid-Open No. 42622/1993).

However, such a resin composition involves problems that it cannot absorb near infrared rays over a wide wavelength region because the near infrared ray-absorption wavelength region of the organic pigment itself is narrow and that this organic pigment is easy to be deteriorated by ultraviolet rays for reasons of its chemical structure, and thus the near infrared ray-absorbing ability of the pigment is lowered, and the initial near infrared ray-absorbing ability of the resin composition cannot be hence retained over a long period of time.

Compositions in which a copper ion is contained as a near infrared ray absorber in an acrylic resin have been known as resin composition having performance that near infrared rays are absorbed (see Japanese Patent Publication No. 5190/1987).

However, such a resin composition involves problems that it is difficult to contain the copper ion in a state sufficiently dispersed in the acrylic resin, and so sufficiently high near infrared ray-absorbing ability cannot be attained, and the transmittance of visible rays is reduced.

It has also been known to add a phosphate group-containing compound such as a phosphate to a synthetic resin to enhance the dispersibility of the copper ion in the synthetic resin (see Japanese Patent Publication No. 5190/1987).

However, such a means involves a problem that since the compatibility of the phosphate group-containing compound with the synthetic resin is not sufficiently high, any resin composition having excellent visible ray-transmitting property is not provided.

DISCLOSURE OF THE INVENTION

The present invention has been made in view of the foregoing circumstances.

It is the first object of the present invention to provide a novel phosphate compound by which a copper ion can be dispersed in a high proportion in a synthetic resin, thereby providing a resin composition which has excellent visible ray-transmitting property and performance that near infrared rays are absorbed with high efficiency, and is little in the deterioration of its near infrared ray-absorbing ability by ultraviolet rays.

The second object of the present invention is to provide a process capable of preparing the novel phosphate compound described above with advantages.

The third object of the present invention is to provide a near infrared ray absorber which contains a copper ion and by which the copper ion can be dispersed in a high proportion in a synthetic resin.

The fourth object of the present invention is to provide a novel phosphate copper compound which has performance that near infrared rays are absorbed with high efficiency, and is little in the deterioration of its near infrared ray-absorbing ability by ultraviolet rays and satisfactory in compatibility with synthetic resins.

The fifth object of the present invention is to provide a process capable of preparing the novel phosphate copper compound described above with advantages.

The sixth object of the present invention is to provide a near infrared ray absorber which is satisfactory in compatibility with synthetic resins and can provide a resin composition which absorbs near infrared rays with high efficiency.

The seventh object of the present invention is to provide a near infrared ray-absorbing acrylic resin composition which has excellent visible ray-transmitting property and performance that near infrared rays are absorbed with high efficiency and is little in the deterioration of its near infrared ray-absorbing ability by ultraviolet rays.

The present inventors have found that a phosphate compound having a specific structure has performance that a copper ion can be dispersed in a high proportion in a synthetic resin, thus leading to completion of the present invention.

A phosphate compound according to the present invention is represented by the following formula (1):

Formula (1)

wherein groups R independently mean a group represented by the following formula (2) or (3), and n is 1 or 2:

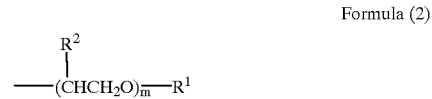

Formula (2)

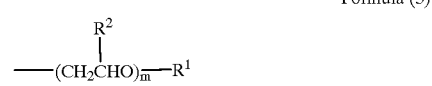

Formula (3)

wherein $R^1$ denotes an alkyl group having 1 to 20 carbon atoms, $R^2$ represents a hydrogen atom or an alkyl group having 1 to 4 carbon atoms, and m is an integer of 1 to 6.

The phosphate compound according to the present invention can be easily prepared in accordance with any one of the following first, second and third processes.

(First Process)

The process comprises reacting an alcohol represented by the following formula (4) or (5) with phosphorus pentoxide:

Formula (4)

$$HO-(\underset{|}{\overset{R^2}{C}}HCH_2O)_{\overline{m}}-R^1$$

Formula (5)

$$HO-(CH_2\underset{|}{\overset{R^2}{C}}HO)_{\overline{m}}-R^1$$

wherein $R^1$ denotes an alkyl group having 1 to 20 carbon atoms, $R^2$ represents a hydrogen atom or an alkyl group having 1 to 4 carbon atoms, and m is an integer of 1 to 6.
(Second Process)

The process comprises reacting the alcohol represented by the formula (4) or (5) with a phosphorus oxyhalide, and hydrolyzing the resultant product.
(Third Process)

The process comprises reacting the alcohol represented by the formula (4) or (5) with phosphorus trihalide, thereby synthesizing a phosphonate compound, and oxidizing the phosphonate compound.

A near infrared ray absorber according to the present invention comprises the phosphate compound represented by the formula (1) and a copper ion;

A phosphate copper compound according to the present invention is obtained by reacting the phosphate compound represented by the formula (1) with a copper salt.

The phosphate copper compound according to the present invention is represented by the following formula (6) or (7):

Formula (6)

$$\underset{RO}{\overset{O}{\underset{\|}{P}}}\overset{O}{\underset{O}{\diagdown}}M$$

Formula (7)

$$\underset{RO}{\overset{O}{\underset{\|}{P}}}\overset{O}{\underset{OR}{\diagdown}}\overset{RO}{\underset{O}{M}}\overset{OR}{\underset{\|}{\diagdown P}}\overset{}{\underset{O}{\diagup}}$$

wherein groups R independently mean a group represented by the following formula (2) or (3), and M denotes a copper ion:

Formula (2)

$$-(\underset{|}{\overset{R^2}{C}}HCH_2O)_{\overline{m}}-R^1$$

Formula (3)

$$-(CH_2\underset{|}{\overset{R^2}{C}}HO)_{\overline{m}}-R^1$$

wherein $R^1$ denotes an alkyl group having 1 to 20 carbon atoms, $R^2$ represents a hydrogen atom or an alkyl group having 1 to 4 carbon atoms, and m is an integer of 1 to 6.

A process for preparing a phosphate copper compound according to the present invention comprises reacting the phosphate compound represented by the formula (1) with a copper salt.

In the preparation process of the phosphate copper compound according to the present invention, the phosphate compound represented by the formula (1) is reacted with the copper salt in an organic solvent, and an acid component formed by the reaction of the phosphate compound with the copper salt and the organic solvent are then removed.

Alternatively, an organic solvent layer containing the phosphate compound represented by the formula (1) and an alkali in an organic solvent insoluble or hardly soluble in water, is brought into contact with a water layer in which the copper salt is dissolved, thereby reacting the phosphate compound with the copper salt, and the organic layer and the water layer are then separated from each other.

A near infrared ray absorber according to the present invention comprises the phosphate copper compound described above as an effective ingredient.

A near infrared ray-absorbing acrylic resin composition according to the present invention comprises an acrylic resin, and the following component (A) and/or component (B) contained in the acrylic resin: Component (A): a component composed of a copper ion and a phosphate compound represented by the formula (1); Component (B): a component composed of a compound obtained by reacting a phosphate compound represented by the formula (1) with a copper salt.

In the near infrared ray-absorbing acrylic resin composition according to the present invention, the component (B) may be composed of the phosphate copper compound represented by the formula (6) or (7).

In the near infrared ray-absorbing acrylic resin composition according to the present invention, it is preferred that the content of the copper ion be 0.1 to 5% by weight based on the total weight of the composition.

In the near infrared ray-absorbing acrylic resin composition according to the present invention, it is preferred that $R^2$ in the formulae (2) and (3) representing the group R in the phosphate compound represented by the formula (1), be a hydrogen atom or an alkyl group having 1 to 4 carbon atoms, and m be an integer of 1 to 6.

The present invention will hereinafter be described in detail.
(Phosphate Compound)

The phosphate compound according to the present invention has a molecular structure represented by the formula (1) as above-mentioned.

In the formula (1) representing the molecular structure of the phosphate compound according to the present invention, R is an alkyl group to which an alkylene oxide group is bonded as indicated by the above formulae (2) and (3).

Here, the recurring number m of the alkylene oxide group is an integer of 1 to 6, preferably 1 to 3. If the value of m exceeds 6, the hardness of a resin composition obtained by containing such a phosphate compound in a synthetic resin is greatly lowered. It is hence not preferable that the value of m exceeds 6. On the other hand, when the value of m is 0, namely, no alkylene oxide group is bonded, the performance of such a phosphate compound that an copper ion is dispersed in a synthetic resin, particularly an acrylic resin is markedly lowered. It is hence not preferable that the value of m is 0.

The phosphate compound according to the present invention may be either a monoester in which the number n of the hydroxyl group in the formula (1) is 2, or a diester in which the number n of the hydroxyl group is 1. When the phosphate compound is a triester in which the value of n is 0, no effect of dispersing a copper ion in a synthetic resin is brought about because the triester has no hydroxyl group capable of being ionically or coordinately bonded to a copper ion.

In the formulae (2) and (3) which represent R in the formula (1), $R^1$ is an alkyl group having 1 to 20, preferably 1 to 10, more preferably 1 to 3 carbon atoms.

If the number of carbon atoms in the alkyl group $R^1$ exceeds 20, it is difficult to disperse a copper ion in a high proportion in a synthetic resin, for example, an acrylic resin.

$R^2$ is a hydrogen atom or an alkyl group having 1 to 4 carbon atoms, preferably an alkyl group having 1 to 4 carbon atoms. More specifically, examples of the alkylene oxide group include ethylene oxide, propylene oxide and butylene oxide groups. Propylene oxide and butylene oxide groups are preferred, with the propylene oxide group being particularly preferred.

If the number of carbon atoms in the alkyl group $R^2$ exceeds 4, it is difficult to disperse a copper ion in a high proportion in a synthetic resin, for example, an acrylic resin.

Specific preferable examples of the phosphate compound according to the present invention include those represented by the following formula (a) to formula (x). Those represented by the following formula (m) to formula (x) are more preferred, with those represented by the following formula (m) to formula (r) being particularly preferred. The phosphate compounds according to the present invention may be used either singly or in any combination thereof.

Formula (a)
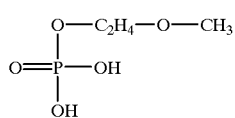

Formula (b)
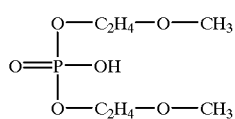

Formula (c)
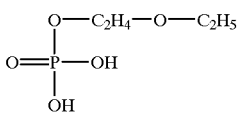

Formula (d)
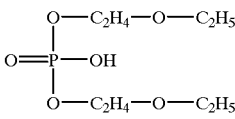

Formula (e)
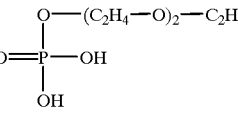

Formula (f)
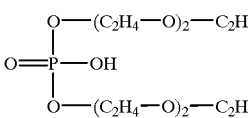

Formula (g)
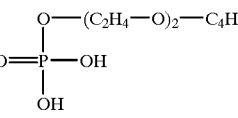

Formula (h)
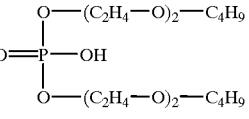

Formula (i)
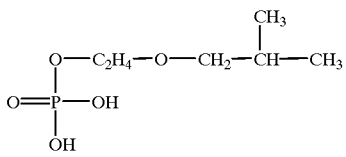

Formula (j)
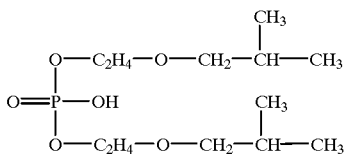

Formula (k)
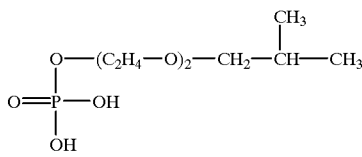

Formula (l)
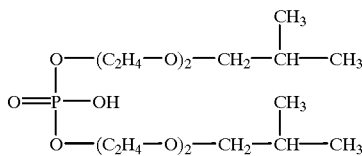

Formula (m)
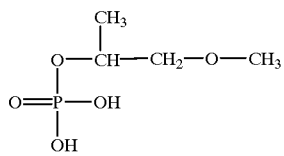

Formula (n)
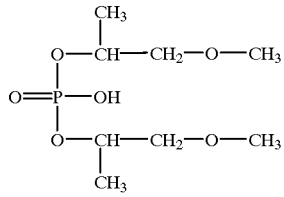

Formula (o)
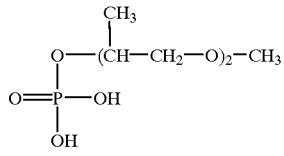

Formula (p)
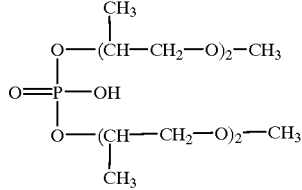

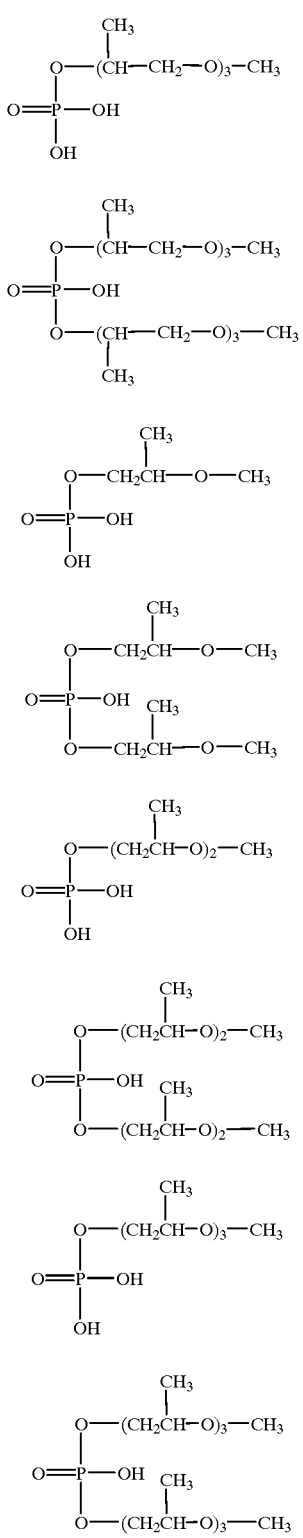

Formula (q)
Formula (r)
Formula (s)
Formula (t)
Formula (u)
Formula (v)
Formula (w)
Formula (x)

The phosphate compounds according to the present invention can be prepared, for example, in accordance with any one of the following first, second and third processes.

[First Process]

The first process is a process comprising reacting an alcohol (hereinafter referred to as the "specific alcohol") represented by the above formula (4) or (5) with phosphorus pentoxide in a proper organic solvent.

The organic solvent used in the reaction of the specific alcohol with phosphorus pentoxide is an organic solvent which does not react with phosphorus pentoxide, and examples thereof include hydrocarbon solvents such as hexane, cyclohexane, heptane, octane, benzene, toluene, xylene and petroleum spirit; halogenated hydrocarbon solvents such as chloroform, carbon tetrachloride, dichloroethane and chlorobenzene; ether solvents such as diethyl ether, diisopropyl ether, dibutyl ether and tetrahydrofuran; and ketone solvents such as acetone, methyl ethyl ketone and dibutyl ketone. Of these, toluene and xylene are preferred.

With respect to conditions for the reaction of the specific alcohol with phosphorus pentoxide, the reaction temperature is 0 to 100° C., preferably 40 to 80° C., and the reaction time is 1 to 24 hours, preferably 4 to 9 hours.

In the first process, the specific alcohol and phosphorus pentoxide are used in proportion that their molar ratio amounts to, for example, 3:1, whereby a mixture containing a phosphate compound (hereinafter may also be referred to as the "monoester") in which the number of the hydroxyl group in the formula (1) is 2, and a phosphate compound (hereinafter may also be referred to as the "diester") in which the number of the hydroxyl group in the formula (1) is 1, in a proportion of about 1:1 can be obtained.

The proportion of the monoester to the diester can be controlled within a range of 99:1 to 40:60 in terms of molar ratio by selecting the proportion of the specific alcohol to phosphorus pentoxide and the reaction conditions.

[Second Process]

The second process is a process comprises reacting the specific alcohol with a phosphorus oxyhalide in a proper organic solvent, and adding water to the resultant product to hydrolyze it.

In this process, it is preferred to use phosphorus oxychloride or phosphorus oxybromide as the phosphorus oxyhalide, with phosphorus oxychloride being particularly preferred.

The organic solvent used in the reaction of the specific alcohol with the phosphorus oxyhalide is an organic solvent which does not react with the phosphorus oxyhalide, and examples thereof include hydrocarbon solvents such as hexane, cyclohexane, heptane, octane, benzene, toluene, xylene and petroleum spirit; halogenated hydrocarbon solvents such as chloroform, carbon tetrachloride, dichloroethane and chlorobenzene; and ether solvents such as diethyl ether, diisopropyl ether and dibutyl ether. Of these, toluene and xylene are preferred.

With respect to conditions for the reaction of the specific alcohol with the phosphorus oxyhalide, the reaction temperature is 0 to 110° C., preferably 40 to 80° C., and the reaction time is 1 to 20 hours, preferably 2 to 8 hours.

In the second process, the specific alcohol and the phosphorus oxyhalide are used in proportions that their molar ratio amounts to, for example, 1:1, whereby a monoester can be obtained.

When the specific alcohol represented by the formula (5) is used, the proportion of the specific alcohol to the phosphorus oxyhalide and reaction conditions are selected, and moreover a Lewis acid catalyst such as titanium tetrachloride (TiCl$_4$), magnesium chloride (MgCl$_2$) or aluminum chloride (AlCl$_3$), and an amine such as triethylamine or tributylamine, or pyridine as a catching agent for hydrochloric acid secondarily produced are preferably used. By using these reaction catalyst and hydrochloride acid-catching agent, a mixture of the monoester and the diester can be provided, and the proportion of the monoester to the diester can be controlled within a range of 99:1 to 1:99 in terms of molar ratio.

When the specific alcohol represented by the above formula (4) is used, the proportion of the specific alcohol to the phosphorus oxyhalide and reaction conditions are selected, and the Lewis acid catalyst and hydrochloride acid-catching agent are used in combination, whereby a mixture of the monoester and the diester can be provided, and the proportion of the monoester to the diester can be controlled within a range of 99:1 to 1:99 in terms of molar ratio.

When an alcohol in which the recurring number m of the alkylene oxide group is small is used as the specific alcohol, however, when a hydrochloric acid-catching agent such as an amine is used, the resulting phosphate compound becomes water-soluble, and accordingly, it may be difficult in some cases to remove an amine hydrochloride formed by cleaning with water.

In the above-described process, the amount of the reaction catalyst used is 0.005 to 0.2 mol, preferably 0.01 to 0.05 mol per mol of the phosphorus oxyhalide.

[Third Process]

The third process is a process comprising reacting the specific alcohol with a phosphorus trihalide in a proper organic solvent, thereby synthesizing a phosphonate compound, and then oxidizing the resultant phosphonate compound.

In this process, phosphorus trichloride or phosphorus tribromide is preferably used as the phosphorus trihalide, with phosphorus trichloride being particularly preferred.

The organic solvent used in the reaction of the specific alcohol with the phosphorus trihalide is an organic solvent which does not react with the phosphorus trihalide, and examples thereof include hydrocarbon solvents such as hexane, cyclohexane, heptane, octane, benzene, toluene, xylene and petroleum spirit; halogenated hydrocarbon solvents such as chloroform, carbon tetrachloride, dichloroethane and chlorobenzene; and ether solvents such as diethyl ether, diisopropyl ether and dibutyl ether. Of these, hexane and heptane are preferred.

With respect to conditions for the reaction of the specific alcohol with the phosphorus trihalide, the reaction temperature is 0 to 90° C., preferably 40 to 75° C., and the reaction time is 1 to 10 hours, preferably 2 to 5 hours.

As a means for oxidizing the phosphonate compound, there may be used a means that a halogen, for example, chlorine gas or the like is reacted with the phosphonate compound, thereby synthesizing a phosphorohaloridate compound, and the phosphorohaloridate compound is hydrolyzed. In this process, the temperature in the reaction of the phosphonate compound with the halogen is preferably 0 to 40° C., particularly preferably 5 to 25° C.

The phosphonate compound may also be purified by distillation before the phosphonate compound is oxidized.

In the third process, the specific alcohol and the phosphorus trihalide are used in proportions that their molar ratio amounts to, for example, 3:1, whereby a diester can be obtained with high purity.

The proportion of the specific alcohol to the phosphorus trihalide and reaction conditions are selected, whereby a mixture of the monoester and the diester can be provided, and the proportion of the monoester to the diester can be controlled within a range of 99:1 to 1:99 in terms of a molar ratio.

The phosphate compounds according to the present invention have high compatibility with synthetic resins, particularly acrylic resins such as (meth)acrylate resins because they have one or more alkoxy groups in their molecular structures. Such a phosphate compound according to the present invention is contained together with a copper ion in an acrylic resin, whereby an ionic bond or coordinate bond is formed between the hydroxyl group in the phosphate compound and the copper ion, with a result that the dispersibility of the copper ion in the acrylic resin is markedly enhanced, and an acrylic resin composition which absorbs near infrared rays with high efficiency is provided by the interaction between the copper ion and the phosphate compound.

<Phosphate Copper Compound>

The phosphate copper compound according to the present invention is obtained by reacting the phosphate compound (hereinafter referred to as the "specific phosphate compound") represented by the formula (1) with a copper salt, and it has, for example, a structure represented by the formula (6) or (7).

In the formula (1) representing the molecular structure of the specific phosphate compound and the formulae (6) and (7) representing the molecular structures of the phosphate copper compounds, R is an alkyl group to which an alkylene oxide group is bonded as indicated by the above formulae (2) and (3).

Here, the recurring number m of the alkylene oxide group is an integer of 1 to 6, preferably 1 to 3. If the value of m exceeds 6, the hardness of a resin composition obtained by containing such a phosphate copper compound in a synthetic resin is greatly lowered. It is hence not preferable that the value of m exceeds 6. On the other hand, when the value of m is 0, namely, no alkylene oxide group is bonded, the dispersibility of the resulting phosphate copper compound in a synthetic resin, particularly an acrylic resin is markedly lowered. It is hence not preferable that the value of m is 0.

In the formulae (2) and (3) representing R, $R^1$ is an alkyl group having 1 to 20, preferably 1 to 10, more preferably 1 to 3 carbon atoms.

If the number of carbon atoms in the alkyl group $R^1$ exceeds 20, it is difficult to disperse the resulting phosphate copper compound in a high proportion in a synthetic resin, for example, an acrylic resin.

$R^2$ is a hydrogen atom or an alkyl group having 1 to 4 carbon atoms. More specifically, examples of the alkylene oxide group include ethylene oxide, propylene oxide and butylene oxide groups, with ethylene oxide and propylene oxide groups being particularly preferred.

If the number of carbon atoms in the alkyl group $R^2$ exceeds 4, it is difficult to disperse the resulting phosphate copper compound in a high proportion in a synthetic resin, and the hardness of the resulting resin composition is greatly lowered. It is hence not preferable that the number of carbon atoms in the alkyl group $R^2$ exceeds 4.

Specific preferable examples of the specific phosphate compound used for obtaining the phosphate copper compound according to the present invention include the compounds represented by the above-described formula (a) to formula (x). The compounds represented by the formula (m) to formula (r) are particularly preferred. These compounds may be used either singly or in any combination thereof.

Examples of the copper salt used for obtaining the phosphate copper compound according to the present invention include anhydrides and hydrates of the copper salts of organic acids, such as copper acetate, copper formate, copper stearate, copper benzoate, copper ethylacetoacetate, copper pyrophosphate, copper naphthenate and copper citrate, and anhydrides and hydrates of the copper salts of inorganic acids, such as copper chloride, copper sulfate, copper nitrate and basic copper carbonate. However, the organic acid salts are preferably used, with copper acetate and copper benzoate being particularly preferred.

The reaction of the specific phosphate compound with the copper salt is performed by bringing the both into contact with each other under proper conditions. Specific examples of such a process include (i) a process comprising mixing the specific phosphate compound with the copper salt to react the both, (ii) a process comprising reacting the specific phosphate compound with the copper salt in a proper organic solvent, and (iii) a process comprising bringing an organic solvent layer containing the specific phosphate compound in an organic solvent into contact with a water layer in which the copper salt is dissolved, thereby reacting the specific phosphate compound with the copper salt.

With respect to conditions for the reaction of the specific phosphate compound with the copper salt, the reaction temperature is 0 to 150° C., preferably 40 to 100° C., and the reaction time is 0.5 to 10 hours, preferably 1 to 7 hours.

The proportion of the copper salt to the specific phosphate compound in the reaction is preferably 0.3 to 1.0 mol per mol of the specific phosphate compound.

No particular limitation is imposed on the organic solvent used in the process (ii) so far as it can dissolve the specific phosphate compound used therein, and examples thereof include aromatic compounds such as benzene, toluene and xylene; alcohols such as methyl alcohol, ethyl alcohol and isopropyl alcohol; glycol ethers such as methyl cellosolve and ethyl cellosolve; ethers such as diethyl ether, diisopropyl ether and dibutyl ether; ketones such as acetone and methyl ethyl ketone; esters such as ethyl acetate; and hexane, kerosene and petroleum ether. Polymerizable organic solvents, such as (meth)acrylic esters such as (meth) acrylates, and aromatic vinyl compounds such as styrene and α-methylstyrene may also be used. Of these, toluene is preferred.

No particular limitation is imposed on the organic solvent used in the process (iii) so far as it is insoluble or hardly soluble in water and can dissolve the specific phosphate compound used therein, and examples thereof include the aromatic compounds, ethers, esters, hexane, kerosene, (meth)acrylic esters and aromatic vinyl compounds among the organic solvents mentioned above as those used in the process (ii). Of these, toluene is preferred.

In the reaction of the specific phosphate compound with the copper salt, an acid component, which is an anion, is isolated from the copper salt. Such an acid component may form the cause that the moisture resistance and heat stability of a synthetic resin, for example, an acrylic resin composition are deteriorated. It is hence preferred that such an acid component be removed as needed.

When the phosphate copper compound is prepared in accordance with the above process (i) or (ii), the formed acid component [the formed acid component and organic solvent in the process (ii)] can be removed by distillation after the specific phosphate compound is reacted with the copper salt.

When the phosphate copper compound is prepared in accordance with the above process (iii), the following process may be mentioned as a preferred process for removing the acid component.

The process comprises adding an alkali to neutralize to an organic solvent layer containing the specific phosphate compound in an organic solvent, which is insoluble or hardly soluble in water, bringing the organic solvent layer into contact with a water layer in which the copper salt is dissolved, thereby reacting the specific phosphate compound with the copper salt, and then separating the organic layer and the water layer from each other.

As examples of the alkali used herein, may be mentioned sodium hydroxide, potassium hydroxide and ammonia. However, the alkali is not limited to these compounds.

According to such a process, a water-soluble salt is formed by the acid component isolated from the copper salt, and the alkali. This salt migrates into the water layer, and the specific phosphate copper compound formed migrates into the organic solvent layer, so that the acid component can be removed by separating the water layer and the organic solvent layer from each other.

The phosphate copper compound according to the present invention can be prepared in the above-described manner. However, the phosphate copper compounds according to the present invention are not limited to the compounds represented by the above formula (6) or (7) so far as they can be obtained by reacting the specific phosphate compound with the copper salt. They may be, for example, those having a structure that copper ions different from each other are bonded to 2 hydroxyl groups in the monoester, those having a structure that a copper ion is bonded to only one of 2 hydroxyl groups in the monoester, those having a structure that a copper ion is bonded to a hydroxyl group in the diester, polymers containing at least two copper ions in their molecules and coordination compounds thereof.

The phosphate copper compounds according to the present invention have performance that near infrared rays are absorbed with high efficiency, and are little in the deterioration of its near infrared ray-absorbing ability by ultraviolet rays and satisfactory in compatibility with synthetic resins, for example, acrylic resins because they have alkoxy group(s) in their molecules.

<Near Infrared Ray Absorber>

The near infrared ray absorbers according to the present invention include those (hereinafter referred to as the "near infrared ray absorber (A)") comprising the phosphate compound represented by the above formula (1) and a copper ion, and those (hereinafter referred to as the "near infrared ray absorber (B)") comprising, as an effective ingredient, the phosphate copper compound obtained by reacting the phosphate compound represented by the above formula (1) with the copper salt. They are added for use into, for example, a synthetic resin or a monomer used for obtaining a synthetic resin.

In the near infrared ray absorber (A), the copper ion is a main component for absorbing near infrared rays and is supplied by a proper copper compound. Specific examples of such a copper compound used as a supply source of the copper ion include those mentioned above as the examples of the copper salt used for obtaining the phosphate copper compound.

The specific phosphate compound is a component for forming a coordinate bond or ionic bond with the copper ion to disperse the copper ion in a synthetic resin. The specific phosphate compounds may be used either singly or in any combination thereof.

With respect to the proportion of the specific phosphate compound to the copper ion in the near infrared ray absorber (A), the hydroxyl group in the phosphate compound is preferably 0.5 to 10 mol, particularly 1.5 to 5 mol per mol of the copper ion. If this proportion is lower than 0.5 mol, it may be difficult in some cases to disperse the copper ion in the synthetic resin. If the proportion exceeds 10 mol, the proportion of the hydroxyl group, which does not participate in forming the coordinate bond or ionic bond with the copper ion becomes excessive, so that a resin composition obtained by adding such a near infrared ray absorber may have high hygroscopic property in some cases.

<Near Infrared Ray-absorbing Acrylic Resin Composition>

The near infrared ray-absorbing acrylic resin compositions according to the present invention comprise an acrylic resin, and any one or both of the following component (A) and component (B) contained in the acrylic resin.

The component (A) is a component composed of a copper ion and a phosphate compound represented by the above formula (1), namely, of the near infrared ray absorber (A) as above, and has a function that near infrared rays are absorbed with high efficiency by the interaction between the copper ion and the specific phosphate compound.

The component (A) may contain metal ion(s) (hereinafter referred to as "other metal ion(s)") other than the copper ion. Specific examples of such other metal ions include ions of metals such as sodium, potassium, calcium, iron, manganese, magnesium and nickel. These other metal ions can be contained in an acrylic resin in a similar manner to the copper ion.

The proportion of such other metal ions used is preferably at most 50% by weight, more preferably at most 30% by weight, most preferably at most 20% by weight based on all metal ions. If the proportion exceeds 50% by weight, it may be difficult in some cases to provide an acrylic resin composition having high near infrared ray absorptivity.

The component (B) is a component composed of a phosphate copper compound (hereinafter referred to as the "specific phosphate copper compound") obtained by reacting a phosphate compound represented by the above formula (1) with a copper salt, namely, of the near infrared ray absorber (B) as above.

In the acrylic resin compositions according to the present invention, the proportion of the copper ion contained is preferably 0.1 to 5% by weight, more preferably 0.3 to 4% by weight, most preferably 0.5 to 3% by weight based on the total weight of each acrylic resin composition.

If this proportion is lower than 0.1% by weight, the performance that near infrared rays are absorbed with high efficiency may not be attained in some cases. If this proportion exceeds 5% by weight on the other hand, it may be difficult in some cases to disperse the metal ion in the acrylic resin, resulting in a failure to provide an acrylic resin composition having excellent visible ray-transmitting property.

As the acrylic resin making up the compositions according to the present invention, there may preferably be used a polymer obtained from a (meth)acrylate monomer.

Specific examples of such a (meth)acrylate monomer include alkyl (meth)acrylates such as methyl (meth)acrylate, ethyl (meth)acrylate, n-propyl (meth)acrylate, n-butyl (meth)acrylate, isobutyl (meth)acrylate, tert-butyl (meth)acrylate, n-hexyl (meth)acrylate and n-octyl (meth)acrylate; modified (meth)acrylates such as glycidyl (meth)acrylate, 2-hydroxyethyl (meth)acrylate, 2-hydroxy-propyl (meth)acrylate, hydroxybutyl (meth)acrylate, isobornyl (meth)acrylate, methoxypolyethylene (meth)acrylate and phenoxyethyl (meth)acrylate; and polyfunctional (meth) acrylates such as ethylene glycol di(meth)acrylate, diethylene glycol di(meth)acrylate, polyethylene glycol di(meth) acrylate, polypropylene glycol di(meth)acrylate, 1,3-butylene glycol di(meth)acrylate, 1,4-butanediol di(meth) acrylate, 1,6-hexanediol di(meth)acrylate, neopentylglycol di(meth)acrylate, 2-hydroxy-1,3-di(meth)acrylate, 2,2-bis [4-(meth)acryloxy-ethoxyphenyl]propane, 2-hydroxy-1-(meth)acryloxy-3-(meth)acryloxypropane, trimethylolpropane tri(meth)acrylate, pentaerythritol tri(meth)acrylate and pentaerythritol tetra(meth)acrylate.

These monomers may be used either singly or in any combination thereof.

The acrylic resin may also be a copolymer of any of the above-mentioned (meth)acrylates and a copolymerizable monomer copolymerizable therewith.

Specific examples of such a copolymerizable monomer include unsaturated carboxylic acids such as (meth)acrylic acid, 2-(meth)acryloyloxyethylsuccinic acid and 2 -(meth) acryloyloxyethylphthalic acid, and aromatic vinyl compounds such as styrene, α-methylstyrene, chlorostyrene, dibromostyrene, methoxystyrene, vinylbenzoic acid and hydroxymethylstyrene.

In the above, a thermoplastic acrylic resin is provided in the case where only monofunctional monomer(s) are used as the monomer(s), while a thermosetting acrylic resin is provided in the case where a polyfunctional monomer is used as a part or the whole of the monomer(s).

In the present invention, the thermoplastic acrylic resin or thermosetting acrylic resin may be chosen for use according to the purpose of use, application field, processing method and the like of the resulting acrylic resin composition.

The acrylic resin compositions according to the present invention are prepared by containing any one or both of the component (A) and component (B) as above in an acrylic resin, and no particular limitation is imposed on the specific process thereof. However, as preferable processes, may be mentioned the following two processes (1) and (2):

Process (1): A process comprising preparing a monomer composition containing a monomer for obtaining an acrylic resin, and any one or both of the specific phosphate compound and copper salt (hereinafter referred to as the "component (A-1)") and the component (B), and subjecting the monomer composition to a radical polymerization treatment. In this process, no particular limitation is imposed on the specific process of the radical polymerization treatment. Any known radical polymerization process making use of a usual radical polymerization initiator, for example, bulk (cast) polymerization, suspension polymerization, emulsion polymerization or solution polymerization process, may be used.

Process (2): A process comprising adding any one or both of the component (A-1) and the component (B) to an acrylic resin to mix them. This process is used when a thermoplastic resin is used as the acrylic resin. This process further includes (i) a process comprising adding any one or both of the component (A-1) and the component (B) to a molten acrylic resin to knead them, and (ii) a process comprising dissolving or swelling an acrylic resin in or with a proper organic solvent, adding any one or both of the component (A-1) and the component (B) to this solution to mix them and then removing the organic solvent from the solution.

Means for kneading the acrylic resin and the component (A-1) and/or the component (B) in the above process (i) include means generally used as melting and kneading methods for thermoplastic resins, for example, melting and kneading means by mixing rolls and means to conduct premixing by a Henschel mixer or the like and then melt and knead the resultant mixture by an extruder.

In the means (ii), no particular limitation is imposed on the organic solvent so far as it can dissolve or swell the acrylic resin used, and specific examples thereof include alcohols such as methyl alcohol, ethyl alcohol and isopropyl alcohol, ketones such as acetone and methyl ethyl ketone, aromatic hydrocarbons such as benzene, toluene and xylene, chlorinated hydrocarbons such as methylene chloride, and amide compounds such as dimethylacrylamide and dimethylformamide.

In the preparation of the acrylic resin compositions, an acid component, which is an anion, is isolated from the copper salt as a result that the specific phosphate compound reacts with the copper salt in the case where the component (A-1) is used. For the same reasons described above, it is preferred that such an acid component be removed as needed.

Processes for removing such an acid component include (a) a process comprising immersing the acrylic resin composition in a proper organic solvent, thereby extracting the acid component, and (b) a process comprising subjecting the monomer composition to a cooling treatment before the monomer composition is subjected to a polymerization treatment, thereby depositing the acid component to remove it.

No particular limitation is imposed on the organic solvent used in the above process (a) so far as it can dissolve the isolated acid component therein and has moderate affinity (affinity to such an extent that it does not dissolve the acrylic resin, but penetrates into the acrylic resin) for the acrylic resin used.

Specific examples of such a solvent include lower aliphatic alcohols such as methyl alcohol, ethyl alcohol, n-propyl alcohol and isopropyl alcohol, ketones such as acetone, methyl ethyl ketone and methyl isobutyl ketone, ethers such as diethyl ether and petroleum ether, aliphatic hydrocarbons and halogenated hydrocarbons such as n-pentane, n-hexane, n-heptane, chloroform, methylene chloride and carbon tetrachloride, and aromatic hydrocarbons such as benzene, toluene and xylene.

As the copper salt making up the component (A-1) in the above process (b), it is preferable to use a salt, the acid component isolated from which is hard to be dissolved in the monomer. Specific examples thereof include the copper salts of carboxylic acids having an aromatic ring, such as benzoic acid.

In the near infrared ray-absorbing acrylic resin compositions according to the present invention, the phosphate residue (residue other than the copper ion) in the specific phosphate compound making up the component (A) or the specific phosphate copper compound making up the component (B) is used in a proportion of, for example, 0.1 to 30 parts by weight, preferably 1 to 20 parts by weight, more preferably 5 to 15 parts by weight per 100 parts by weight of the acrylic resin.

The acrylic resin compositions obtained in such a manner contain the copper ion in a state sufficiently dispersed in the acrylic resin. Therefore, they have excellent visible ray-transmitting property and performance that near infrared rays are absorbed with high efficiency, are little in the deterioration of their near infrared ray-absorbing ability by ultraviolet rays and can be formed or molded into desired shapes such as plates, columns and lenses.

Accordingly, the acrylic resin compositions according to the present invention are suitable for use as materials for constructing various optical products such as heat ray-absorbing window members, near infrared ray-cutting filters and near infrared ray-cutting lenses.

BEST MODE FOR CARRYING OUT THE INVENTION

The present invention will hereinafter be described specifically by the following examples. However, the present invention is not limited by these examples.

EXAMPLE 1

A four-necked flask was equipped with a stirrer, a thermometer and a condenser and charged with 1-methoxy-2-propanol (270 g; 3.0 mol) and toluene (400 g) as a solvent, and the resultant mixture was cooled to 5° C. with stirring. Phosphorus pentoxide (142 g; 1.0 mol) was then gradually added to the resultant solution while keeping the temperature of the solution at 5 to 10° C. Thereafter, the temperature of the solution was gradually raised to react 1-methoxy-2-propanol with phosphorus pentoxide under conditions of 60° C. and 6 hours. Water (20 g) was added to the resultant reaction mixture, and the resultant mixture was stirred at 80° C. for 2 hours. After the condenser installed in the four-necked flask was replaced by a distiller, toluene and water contained in the reaction mixture were removed by the distiller, thereby obtaining a liquid reaction product (390 g).

Figure 1:
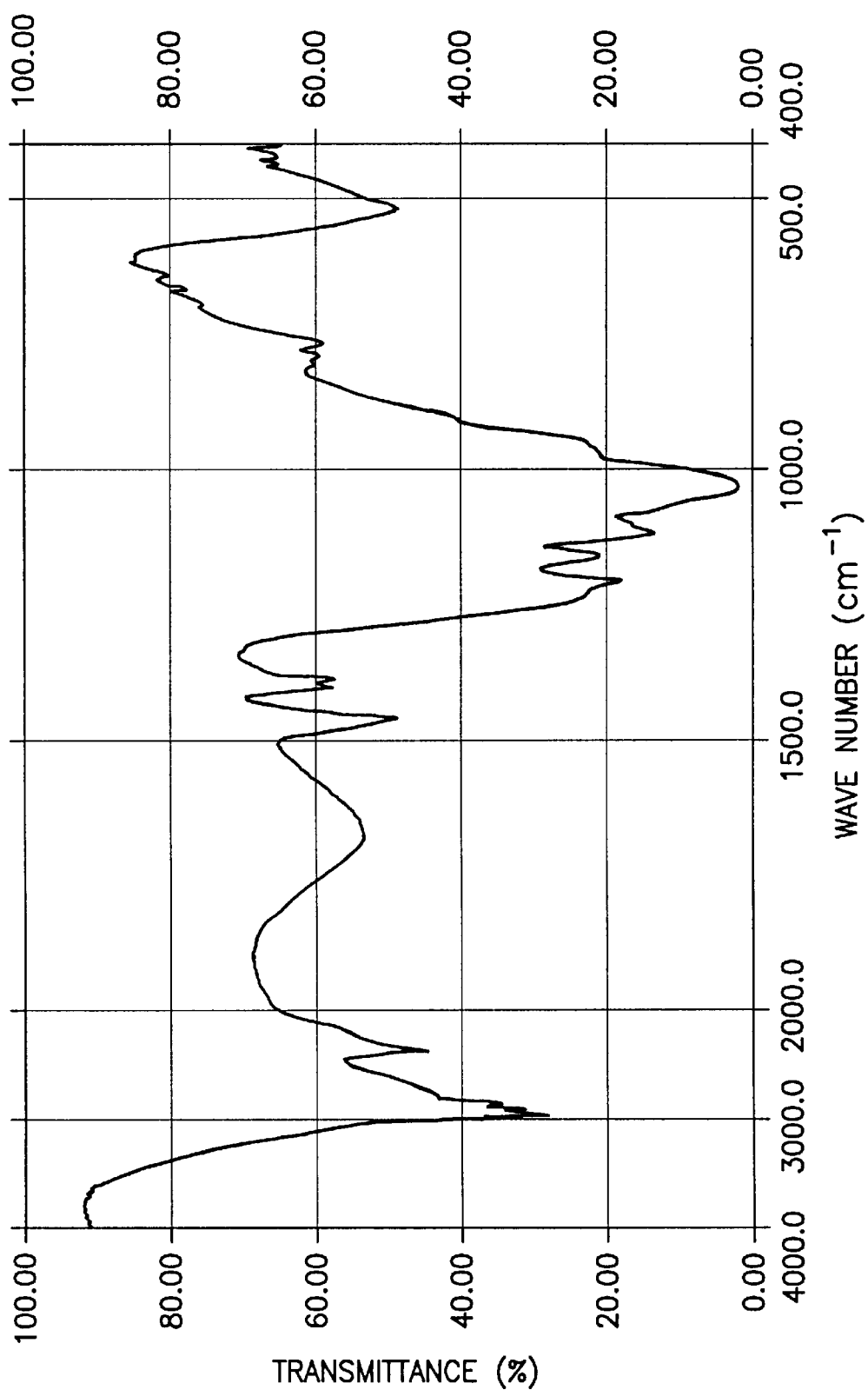
FIG. 1 diagrammatically illustrates an infrared spectral curve of a phosphate compound obtained in the following Example 1.

With respect to the reaction product thus obtained, spectroscopic analysis was performed by an infrared absorption spectrum. As a result, it was confirmed that the reaction product contains a phosphate compound represented by the formula (m) and a phosphate compound represented by the formula (n). The infrared absorption curve of this reaction product is illustrated in FIG. 1.

With respect to the reaction product thus obtained, the compositions and yield of the phosphate compounds were calculated out in the following manner.

[Composition of Phosphate Compounds]

An Autotitrator COMTITE-101 manufactured by Hiranuma Sangyo K. K. was used to conduct neutralization titration of the reaction product, and the contents of the phosphate compound represented by the formula (m) and the phosphate compound represented by the formula (n) were respectively calculated out from the titers at the resultant first inflection point and second inflection point. The results are shown in Table 1.

[Yield]

Concentrated nitric acid and perchloric acid were added to the reaction product and the reaction product was decomposed under heat. After distilled water was added to the decomposition product to dilute it, nitric acid, a 0.25% aqueous solution of ammonium vanadate and a 5% aqueous solution of ammonium molybdate were added to the resultant solution to develop a color, thereby measuring an absorbance at a wavelength of 440 nm by means of a spectrophotometer to find a concentration (% by weight) of phosphorus in the reaction products based on the absorbance of a standard solution of phosphorus.

The yield was calculated out from this concentration of phosphorus and a concentration (% by weight) of phosphorus in the phosphorus compound used. The result is shown in Table 1.

EXAMPLE 2

A four-necked flask was equipped with a stirrer, a thermometer, a condenser to which a water scrubber had been connected, and a dropping funnel, and charged with phosphorus oxychloride (153 g; 1.0 mol), titanium tetrachloride (4.6 g) as a catalyst and toluene (180 g) as a solvent, and the resultant mixture was cooled to 5° C. with stirring. After 1-methoxy-2-propanol (180 g; 2.0 mol) was added to the resultant solution, triethylamine (202 g; 2.0 mol) was added to the solution over 2 hours while keeping the temperature of the solution at 5 to 15° C. The temperature of the solution was gradually raised to react 1-methoxy-2-propanol with phosphorus oxychloride under conditions of 50° C. and 2 hours. Water (200 g) was then added to the resultant reaction mixture and hydrolysis of the reaction product was conducted under conditions of 50° C. and 1 hour. The resultant reaction mixture was left at rest, thereby separating the reaction mixture into a toluene layer and a water layer. Thereafter, the toluene solution was recovered. Toluene (100 g) was then added to the residual aqueous solution to conduct an extraction treatment of the reaction product contained in the aqueous solution, and a toluene solution was recovered. This process was conducted repeatedly 3 times, thereby recovering the toluene solution in an amount of 600 g in total. After the condenser installed in the four-necked flask was replaced by a distiller, a treatment for removing toluene and the like from the toluene solution was conducted by this distiller, thereby obtaining a liquid reaction product (165 g).

Figure 2:
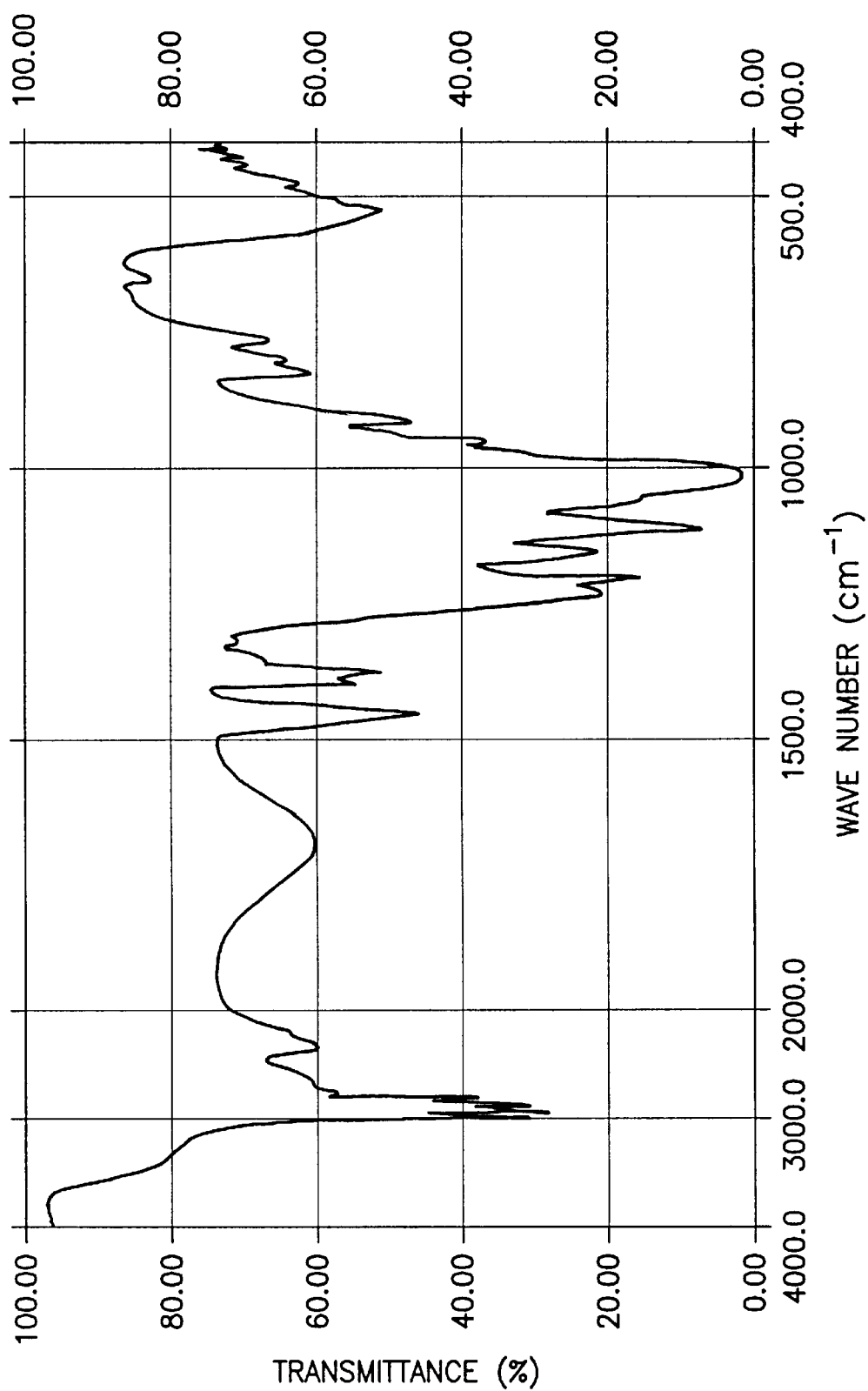
FIG. 2 diagrammatically illustrates an infrared spectral curve of a phosphate compound obtained in the following Example 2.

With respect to the reaction product thus obtained, spectroscopic analysis was performed by an infrared absorption spectrum. As a result, it was confirmed that the reaction product contains a phosphate compound represented by the formula (m) and a phosphate compound represented by the formula (n). The infrared absorption curve of this reaction product is illustrated in FIG. 2.

With respect to the reaction product thus obtained, the composition and yield of the phosphate compounds were calculated out in the same manner as in Example 1. The results are shown in Table 1.

EXAMPLE 3

(1) Preparation of Phosphonate Compound

A four-necked flask was equipped with a stirrer, a thermometer, a condenser to which a water scrubber had been connected, and a dropping funnel, and charged with phosphorus trichloride (275 g; 2.0 mol) and hexane (200 g) as a solvent, and the resultant mixture was heated to 50° C. 1-Methoxy-2-propanol (540 g; 6.0 mol) was then added to the resultant solution over 2 hours while keeping the temperature of the solution at 50 to 70° C. Hydrogen chloride generated upon the addition of 1-methoxy-2-propanol in the above-described process was introduced into the water scrubber to recover it. After completion of the addition of 1-methoxy-2-propanol, the interior of the four-necked flask was sucked at 60° C. for 1 hour under a reduced pressure of 500 mmHg, thereby conducting a treatment for removing remaining hydrogen chloride. After the condenser installed in the four-necked flask was replaced by a distiller, a treatment for removing hexane and 1-methoxy-2-chloropropane, which was a reaction by-product, in the reaction mixture was conducted by this distiller. The residue was further distilled under reduced pressure, and a distillate at 119.0 to 125.0° C. under 3 mmHg was recovered, thereby obtaining a liquid product (398 g). This liquid product was analyzed by gas chromatography. As a result, the purity (calculated out by an area ratio in a chart) of the bis(2-methoxy-1-methylethyl) hydrogen-phosphonate was 96.3%.

(2) Preparation of Phosphate Compound

A four-necked flask was equipped with a stirrer, a thermometer, a condenser to which a 5% aqueous sodium hydroxide scrubber had been connected, and a dip tube for introducing chlorine gas, and charged with the above-obtained liquid product (226 g; about 1.0 mol as bis(2-methoxy-1-methylethyl) hydrogenphosphonate), and the contents were cooled to 10° C. Chlorine gas was blown into bis(2-methoxy-1-methylethyl) hydrogenphosphonate while the temperature thereof was kept at 10 to 20° C., and the introduction of chlorine gas was continued until the solution was slightly colored yellow. Thereafter, the interior of the four-necked flask was sucked at 25° C. under a reduced pressure of 15 mmHg, thereby conducting a treatment for removing excess chlorine gas and hydrogen chloride, which was a reaction by-product, to obtain a liquid product (263 g). This liquid product was analyzed by gas chromatography. As a result, the purity (calculated out by an area ratio in a chart) of the bis(2-methoxy-1-methylethyl) phosphorochloridate was 92.4%. A concentration of chlorine in the liquid product was measured in accordance with "Determination Method of Chloride Ion by Silver Nitrate Standard Solution" described in "Experimental Methods of Analytical Chemistry" (published by Kagakudojin K. K.). As a result, the concentration of chlorine was 14.3%.

Water (90 g; 5.0 mol) was added to the resultant liquid product, and the temperature of this solution was gradually raised to conduct hydrolysis of bis(2-methoxy-1-methylethyl) phosphorochloridate under conditions of 40° C. and 2 hours. After the condenser installed in the four-necked flask was replaced by a distiller, a treatment for removing water from the reaction mixture was conducted by this distiller, thereby obtaining a reaction product (234 g).

Figure 3:
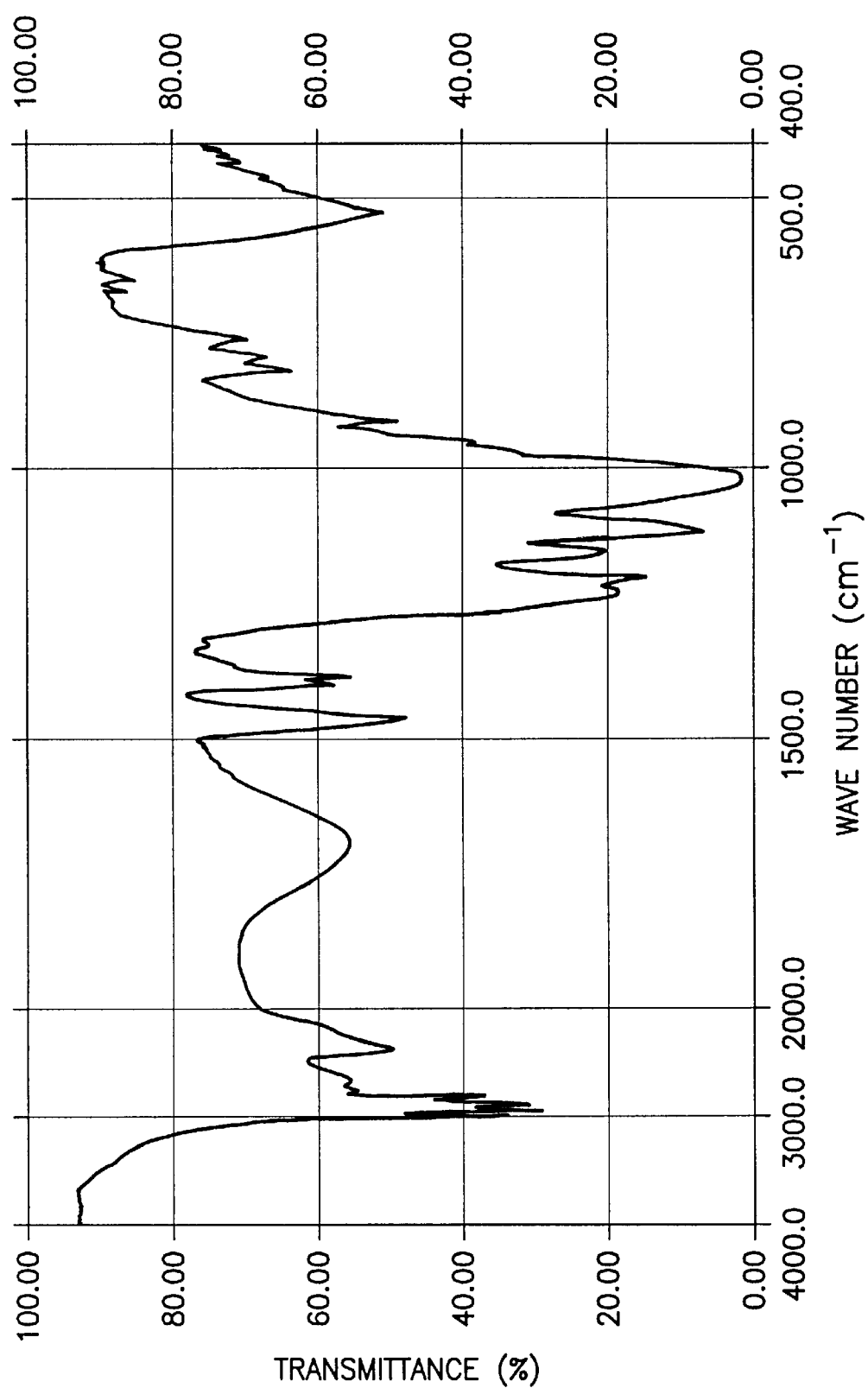
FIG. 3 diagrammatically illustrates an infrared spectral curve of a phosphate compound obtained in the following Example 3.

With respect to the reaction product thus obtained, spectroscopic analysis was performed by an infrared absorption spectrum. As a result, it was confirmed that the reaction product contains a phosphate compound represented by the formula (m) and a phosphate compound represented by the formula (n). The infrared absorption curve of this reaction product is illustrated in FIG. 3.

With respect to the reaction product thus obtained, the composition and yield of the phosphate compounds were calculated out in the same manner as in Example 1. The results are shown in Table 1.

EXAMPLE 4

(1) Preparation of Phosphonate Compound

A four-necked flask was equipped with a stirrer, a thermometer, a condenser to which a water scrubber had been connected, and a dropping funnel, and charged with phosphorus trichloride (137.5 g; 1.0 mol) and hexane (300 g) as a solvent, and the resultant mixture was heated to 50° C. Dipropylene glycol monomethyl ether (444 g; 3.0 mol)

was then added to the resultant solution over 2 hours while keeping the temperature of the solution at 50 to 70° C. Hydrogen chloride generated upon the addition of dipropylene glycol monomethyl ether in the above-described process was introduced into the water scrubber to recover it. After completion of the addition of dipropylene glycol monomethyl ether, the interior of the four-necked flask was sucked at 60° C. for 3 hours under a reduced pressure of 500 mmHg, thereby conducting a treatment for removing remaining hydrogen chloride. After the condenser installed in the four-necked flask was replaced by a distiller, a treatment for removing hexane in the reaction mixture was conducted by this distiller, thereby obtaining a liquid mixture (504 g) of a phosphonate compound of dipropylene glycol monomethyl ether and a chloride of dipropylene glycol monomethyl ether, which was a reaction by-product. This liquid mixture was analyzed by gel permeation chromatography. As a result, the purity (calculated out by an area ratio in a chart) of the phosphonate compound was 72.2%.

(2) Preparation of Phosphate Compound

A four-necked flask was equipped with a stirrer, a thermometer, a condenser to which a 5% aqueous sodium hydroxide scrubber had been connected, and a dip tube for introducing chlorine gas, and charged with the above-obtained liquid mixture (504 g), and the contents were cooled to 10° C. Chlorine gas was blown into this liquid mixture while the temperature thereof was kept at 10 to 20° C., and the introduction of chlorine gas was continued until the solution was slightly colored yellow. Thereafter, the interior of the four-necked flask was sucked at 25° C. under a reduced pressure of 15 mmHg, thereby conducting a treatment for removing excess chlorine gas and hydrogen chloride, which was a reaction by-product, to obtain a mixture (546 g) of a phosphorochloridate of dipropylene glycol monomethyl ether and a chloride of dipropylene glycol monomethyl ether. This mixture was analyzed by gel permeation chromatography. As a result, the purity (calculated out by an area ratio in a chart) of the phosphorochloridate was 69.9%. A concentration of chlorine in the mixture was measured in the same manner as in Example 3. As a result, the concentration of chlorine was 9.3%.

Water (128 g; 7.0 mol) was added to the resultant mixture, and the temperature of this solution was gradually raised to conduct hydrolysis of the phosphorochloridate of dipropylene glycol monomethyl ether under conditions of 50° C. and 2 hours. After the condenser installed in the four-necked flask was replaced by a distiller, steam distillation was conducted by this distiller under a reduced pressure or 20 mmHg while introducing steam from the dip tube, thereby conducting a treatment for removing water and the chloride of dipropylene glycol monomethyl ether from the reaction liquid to obtain a reaction product (348 g).

Figure 4:
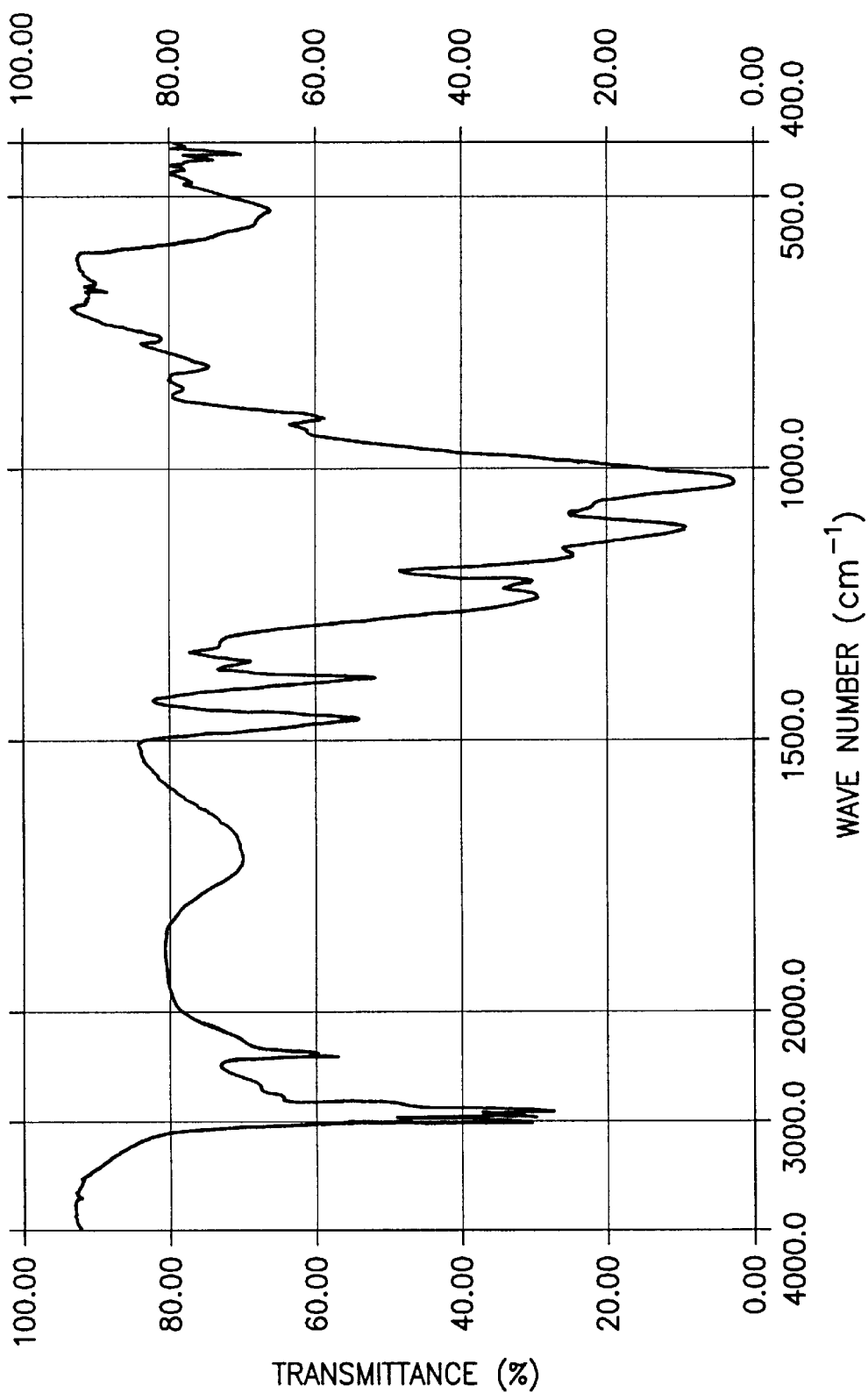
FIG. 4 diagrammatically illustrates an infrared spectral curve of a phosphate compound obtained in the following Example 4.

With respect to the reaction product thus obtained, spectroscopic analysis was performed by an infrared absorption spectrum. As a result, it was confirmed that the reaction product contains a phosphate compound represented by the formula (o) and a phosphate compound represented by the formula (p). The infrared absorption curve of this reaction product is illustrated in FIG. 4.

With respect to the reaction product thus obtained, the composition and yield of the phosphate compounds were calculated out in the same manner as in Example 1. The results are shown in Table 1.

EXAMPLE 5

A process was performed in the same manner as in Example 4 except that tripropylene glycol monomethyl ether (3.0 mol) was used in place of dipropylene glycol monomethyl ether, thereby obtaining a reaction product (424 g).

Figure 5:
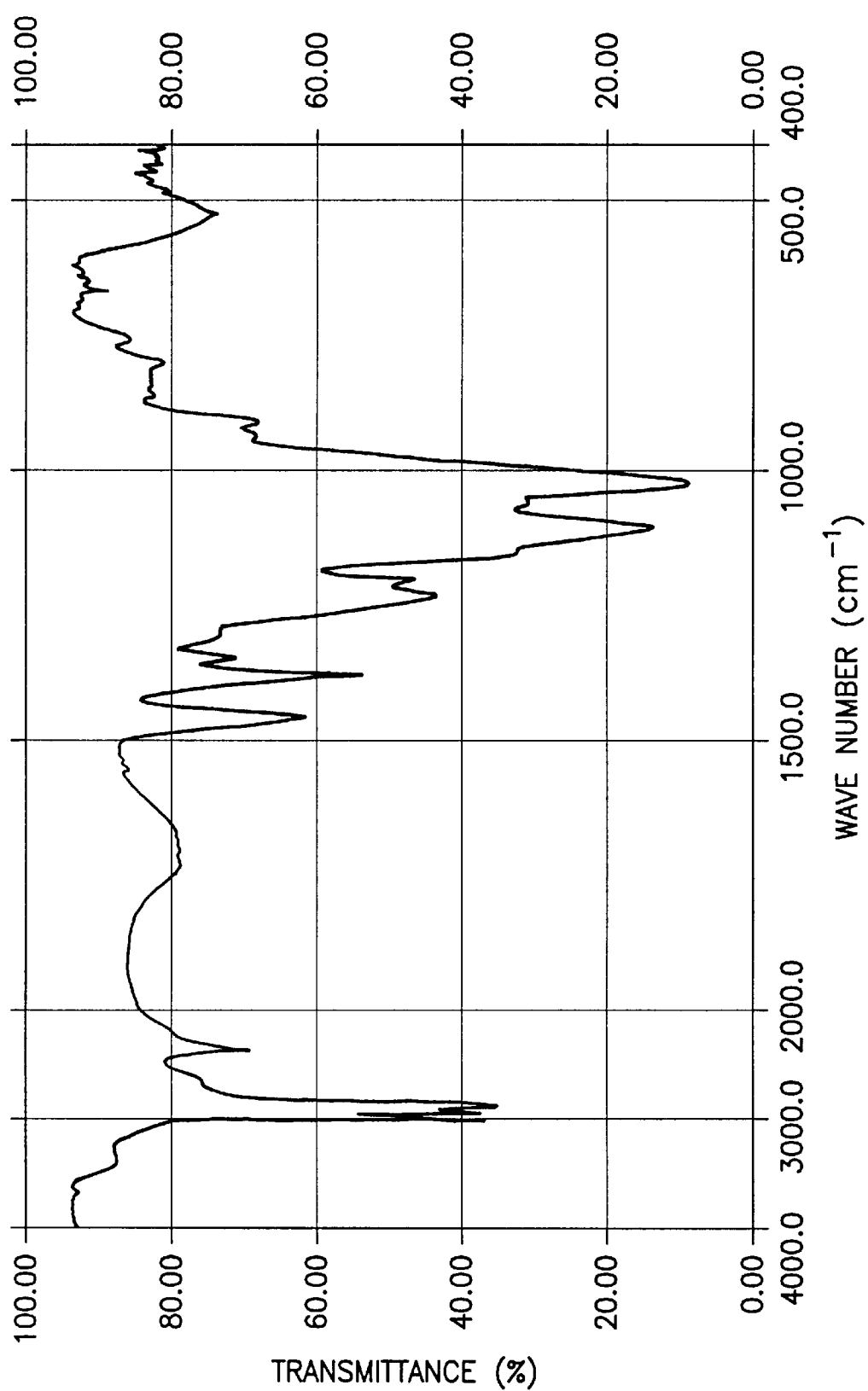
FIG. 5 diagrammatically illustrates an infrared spectral curve of a phosphate compound obtained in the following Example 5.

With respect to the reaction product thus obtained, spectroscopic analysis was performed by an infrared absorption spectrum. As a result, it was confirmed that the reaction product contains a phosphate compound represented by the formula (q) and a phosphate compound represented by the formula (r). The infrared absorption curve of this reaction product is illustrated in FIG. 5.

With respect to the reaction product thus obtained, the composition and yield of the phosphate compounds were calculated out in the same manner as in Example 1. The results are shown in Table 1.

TABLE 1

| | Composition of phosphate compounds (% by weight) | | Concentration of phosphorus | |
|---|---|---|---|---|
| | Monoester | Diester | (% by weight) | Yield (%) |
| Ex. 1 | 47.1 | 49.1 | 15.2 | 95.7 |
| Ex. 2 | 1.2 | 85.8 | 12.0 | 63.9 |
| Ex. 3 | 3.8 | 91.6 | 13.0 | 86.4 |
| Ex. 4 | 0.6 | 96.8 | 8.5 | 95.2 |
| Ex. 5 | 3.4 | 86.4 | 6.5 | 88.9 |

<Preparation of Resin Composition>

The phosphate compound (hereinafter referred to as "Ester A") obtained in Example 3, the phosphate compound (hereinafter referred to as "Ester B") obtained in Example 4 and the phosphate compound (hereinafter referred to as "Ester C") obtained in Example 5 were separately used to prepare resin compositions in the following manner.

The phosphate compound and methyl methacrylate were mixed in accordance with their corresponding formulations shown in Table 2. Anhydrous copper benzoate was added to the resultant mixtures, and stirring and mixing were conducted at 60° C. for 1 hour, thereby preparing monomer compositions. t-Butyl peroxypivalate (0.2 g) was added to the monomer compositions, and the resultant mixtures were successively heated at different temperatures of 45° C. for 16 hours, 60° C. for 8 hours and 90° C. for 3 hours to polymerize the methyl methacrylate, thereby preparing resin compositions (1) to (3) containing respective near infrared ray absorbers (phosphate compound and copper ion) according to the present invention.

<Evaluation of Resin Composition>

The resin compositions (1) to (3) thus obtained were press-molded at 200° C., thereby obtaining blue and transparent plates having a thickness of 4 mm.

With respect to the plates thus obtained, the light transmittances at wavelengths of 550 nm, 800 nm and 900 nm were measured.

The plates thus obtained were subjected to a 500-hour weathering test by means of a sunshine weathermeter (black panel temperature: 63° C., precipitated), and the light transmittances of the plates after the test were measured to investigate the plates as to whether the light transmittances were changed or not.

The results are shown in Table 2.

TABLE 2

|  |  | Resin composition | | |
|---|---|---|---|---|
|  |  | (1) | (2) | (3) |
| Formulation of monomer composition (g) | Ester A | 1 | | |
|  | Ester B | | 1 | |
|  | Ester C | | | 1 |
|  | Methyl methacrylate | 20 | 20 | 20 |
|  | Anhydrous copper benzoate | 0.48 | 0.37 | 0.32 |
| Light transmittance | Wavelength of 550 nm (%) | 85 | 81 | 79 |
|  | Wavelength of 800 nm (%) | 8 | 10 | 9 |
|  | Wavelength of 900 nm (%) | 5 | 16 | 14 |
| Change in light transmittance after weathering test | | None | None | None |

As apparent from the results shown in Table 2, it was confirmed that the resin compositions (1) to (3) containing the respective near infrared ray absorbers according to the present invention have excellent visible ray-transmitting property and performance that near infrared rays are absorbed with high efficiency, and are little in the deterioration of their near infrared ray-absorbing ability by ultraviolet rays.

EXAMPLE 6

The compound (0.14 g) represented by the above formula (a) and the compound (0.80 g) represented by the above formula (b) as specific phosphate compounds were added into methyl methacrylate (20 g) to mix them. Anhydrous copper benzoate (1.17 g) was added to the mixture solution, and the resultant mixture was stirred at 60° C. for 1 hour, thereby reacting the phosphate compounds with anhydrous copper benzoate to prepare a monomer composition containing the specific phosphate copper compounds.

t-Butyl peroxypivalate (0.2 g) was added to the monomer composition thus obtained, and the resultant mixture was successively heated at different temperatures of 45° C. for 16 hours, 60° C. for 8 hours and 90° C. for 3 hours to polymerize the methyl methacrylate, thereby preparing an acrylic resin composition.

The acrylic resin composition obtained in the above-described manner was evaluated.

The acrylic resin composition was press-molded at 200° C., thereby obtaining a blue and transparent plate having a thickness of 4 mm.

With respect to the plate thus obtained, the light transmittances at wavelengths of 550 nm, 800 nm and 900 nm were measured.

The plate thus obtained was subjected to a 500-hour weathering test by means of a sunshine weathermeter (black panel temperature: 63° C., precipitated), and the light transmittances of the plate after the test were measured to investigate the plate as to whether the light transmittances were changed or not.

The results are shown in Table 3.

Figure 6:
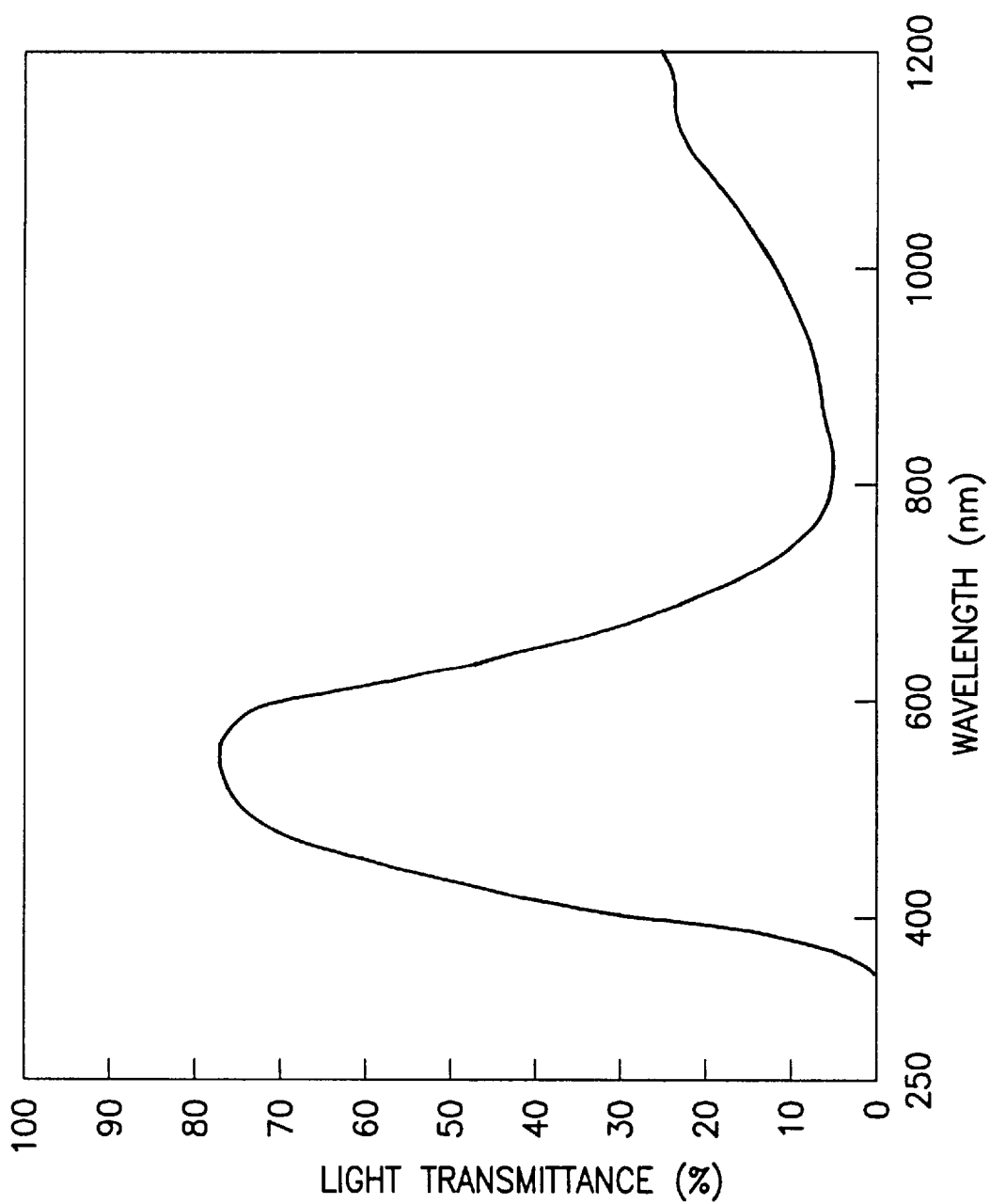
FIG. 6 diagrammatically illustrates a spectral transmittance curve of a near infrared ray-absorbing acrylic resin composition obtained in the following Example 6.

The spectral transmittance curve of the plate is illustrated in FIG. 6.

EXAMPLE 7 to EXAMPLE 17

The compounds represented by the above formula (a) to the formula (r) were provided as specific phosphate compounds (these compounds will hereinafter be referred to as "Ester (a)" to "Ester (r)", respectively) to perform a process in the same manner as in Example 6 except that the specific phosphate compounds and copper salts were used in accordance with their corresponding formulations shown in following Table 3, thereby preparing acrylic resin compositions to evaluate them.

The results are shown in Table 3.

TABLE 3

|  | Example | | | | | | | | | | | |
|---|---|---|---|---|---|---|---|---|---|---|---|---|
|  | 6 | 7 | 8 | 9 | 10 | 11 | 12 | 13 | 14 | 15 | 16 | 17 |
| Formulation of monomer composition (g) | | | | | | | | | | | | |
| Ester (a) | 0.14 | 0.14 | | | | | | | | | | 0.42 |
| Ester (b) | 0.80 | 0.80 | | | | | | | | | | 2.40 |
| Ester (c) | | | 0.20 | | | | | | | | | |
| Ester (d) | | | 0.80 | | | | | | | | | |
| Ester (e) | | | | 0.41 | 0.41 | | | | | | | |
| Ester (f) | | | | 0.53 | 0.53 | | | | | | | |
| Ester (g) | | | | | | 0.80 | | | | | | |
| Ester (h) | | | | | | 0.80 | | | | | | |
| Ester (i) | | | | | | | 0.14 | | | | | |
| Ester (j) | | | | | | | 0.86 | | | | | |
| Ester (k) | | | | | | | | 0.08 | | | | |
| Ester (l) | | | | | | | | 0.42 | | | | |
| Ester (m) | | | | | | | | | 0.012 | | | |
| Ester (n) | | | | | | | | | 0.86 | | | |
| Ester (o) | | | | | | | | | | 0.016 | | |
| Ester (p) | | | | | | | | | | 0.86 | | |
| Ester (q) | | | | | | | | | | | 0.016 | |
| Ester (r) | | | | | | | | | | | 0.80 | |
| Methyl methacrylate | 20 | 20 | 20 | 20 | 20 | 20 | 20 | 20 | 20 | 20 | 20 | 20 |
| Anhydrous copper benzoate | 1.17 | 0.49 | 0.63 | 0.47 | 1.08 | | | | 0.48 | 0.37 | 0.32 | 3.60 |
| Anhydrous copper acetate monohydrate | | | | | | 0.34 | 0.39 | 0.16 | | | | |
| Content of copper ion | 1.06 | 0.46 | 0.58 | 0.44 | 0.98 | 0.54 | 0.64 | 0.27 | 0.45 | 0.35 | 0.30 | 2.71 |

TABLE 3-continued

| | Example | | | | | | | | | | | |
|---|---|---|---|---|---|---|---|---|---|---|---|---|
| | 6 | 7 | 8 | 9 | 10 | 11 | 12 | 13 | 14 | 15 | 16 | 17 |
| (% by weight) Light transmittance | | | | | | | | | | | | |
| Wavelength of 550 nm (%) | >70 | >70 | >70 | >70 | >70 | >70 | >70 | >70 | >70 | >70 | >70 | >70 |
| Wavelength of 800 nm (%) | 7 | 2 | 5 | 2 | 8 | 8 | 7 | 17 | 8 | 10 | 9 | 1 |
| Wavelength of 900 nm (%) | 10 | 3 | 8 | 6 | 12 | 15 | 14 | 28 | 15 | 16 | 14 | 2 |
| Change in light transmittance after weathering test | None | None | None | None | None | None | None | None | None | None | None | None |

EXAMPLE 18

A four-necked flask was equipped with a stirrer, a thermometer and a condenser and charged with Ester (n) (242 g; 1.0 mol) as the specific phosphate compound, toluene (250 g) as a solvent and copper acetate monohydrate (100 g; 0.5 mol). The temperature of the mixture was gradually raised, and the mixture was stirred at 40° C. for 1 hour and further at 80° C. for 3 hours, thereby reacting the specific phosphate compound with copper acetate monohydrate to obtain a blue and transparent solution. The solution was subjected to a distillation treatment to remove acetic acid formed by the reaction of the specific phosphate compound with copper acetate monohydrate and toluene, thereby obtaining a phosphate copper compound (270 g) according to the present invention. The yield was 99.0%.

Figure 7:
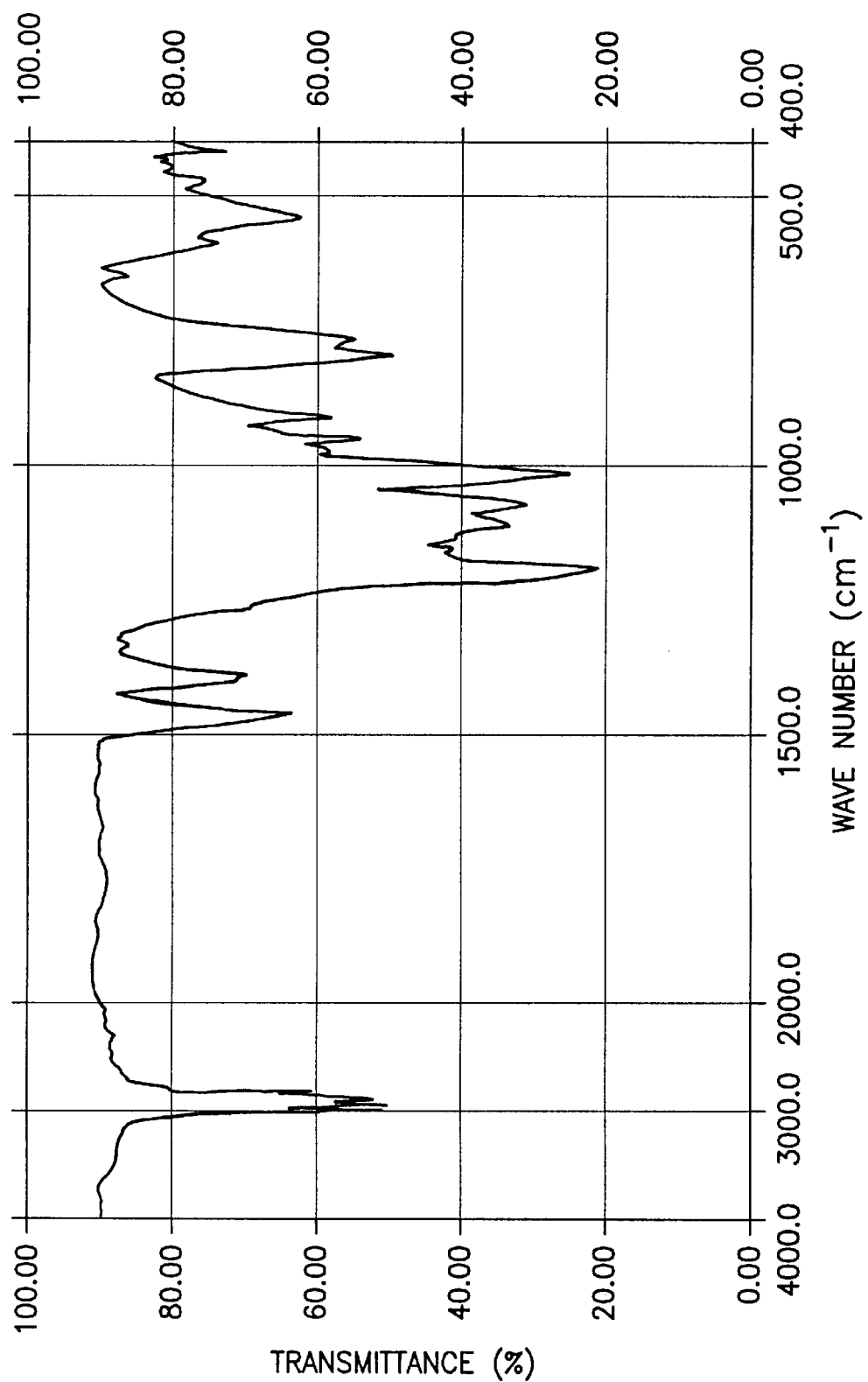
FIG. 7 diagrammatically illustrates an infrared spectral curve of a phosphate copper compound obtained in the following Example 18.

The thus-obtained phosphate copper compound had a structure represented by the following formula (8). The phosphate copper compound was analyzed. As a result, the content of phosphorus was 11.40% by weight (theoretical value: 11.35% by weight), and the content of copper was 11.70% by weight (theoretical value: 11.64% by weight). This compound had no clear melting point, and its decomposition temperature was 247° C. Incidentally, the infrared absorption curve of the phosphate copper compound thus obtained is illustrated in FIG. 7.

EXAMPLE 19

A four-necked flask was equipped with a stirrer, a thermometer and a condenser and charged with Ester (p) (358 g; 1.0 mol) as the specific phosphate compound, toluene (360 g) as a solvent and copper acetate monohydrate (100 g; 0.5 mol). The temperature of the mixture was gradually raised, and the mixture was stirred at 40° C. for 1 hour and further at 80° C. for 3 hours, thereby reacting the specific phosphate compound with copper acetate monohydrate to obtain a blue and transparent solution. The solution was subjected to a distillation treatment to remove acetic acid formed by the reaction of the specific phosphate compound with copper acetate monohydrate and toluene, thereby obtaining a phosphate copper compound (355 g) according to the present invention. The yield was 91.3%.

Figure 8:
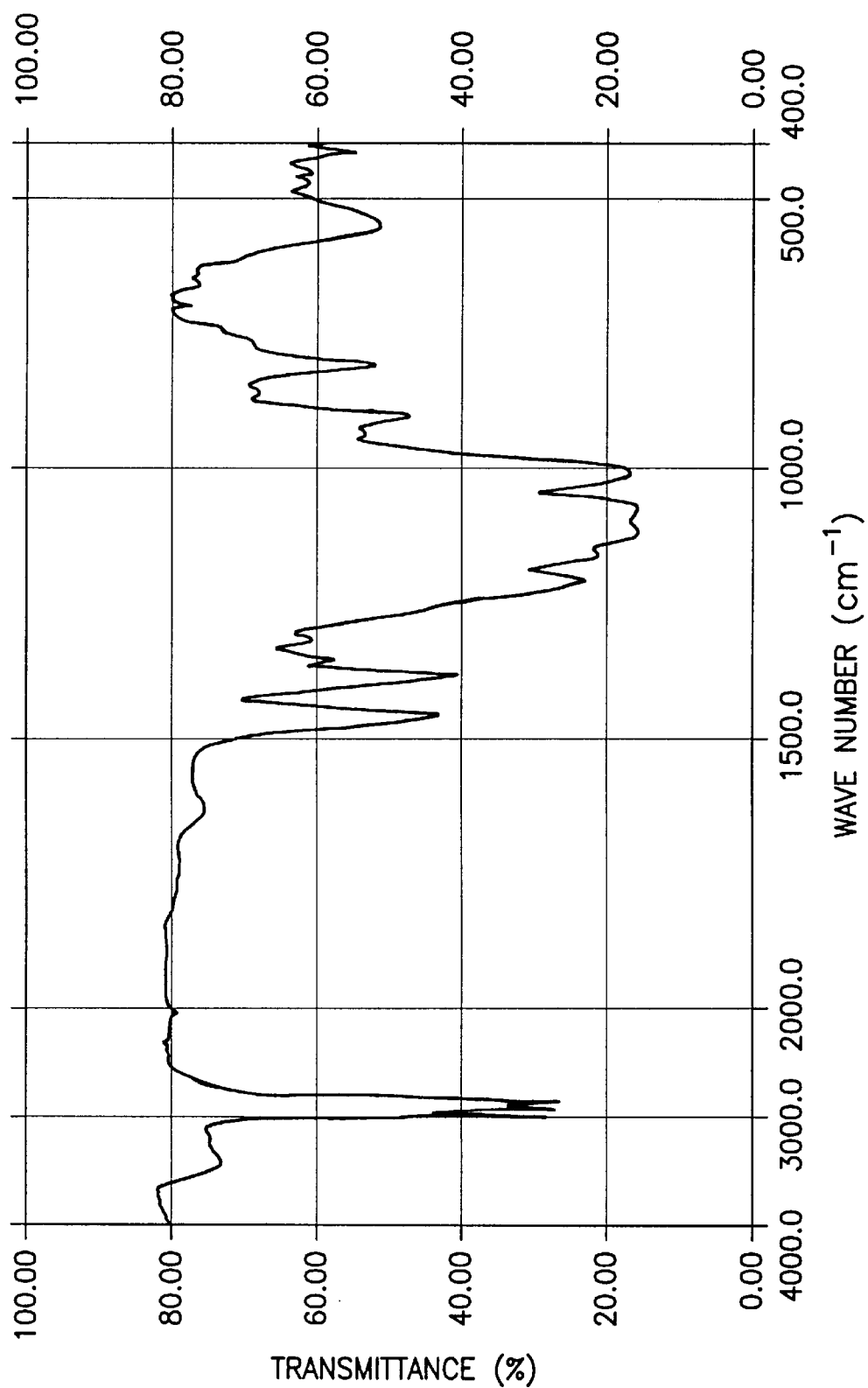
FIG. 8 diagrammatically illustrates an infrared spectral curve of a phosphate copper compound obtained in the following Example 19.

The thus-obtained phosphate copper compound had a structure represented by the following formula (9) and was in the form of a jelly solid. The phosphate copper compound was analyzed. As a result, the content of phosphorus was 8.03% by weight (theoretical value: 7.96% by weight), and the content of copper was 8.20% by weight (theoretical value: 8.17% by weight). Incidentally, the infrared absorption curve of the phosphate copper compound thus obtained is illustrated in FIG. 8.

Formula (8)

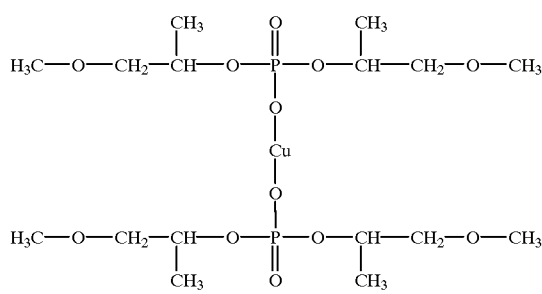

Formula (9)

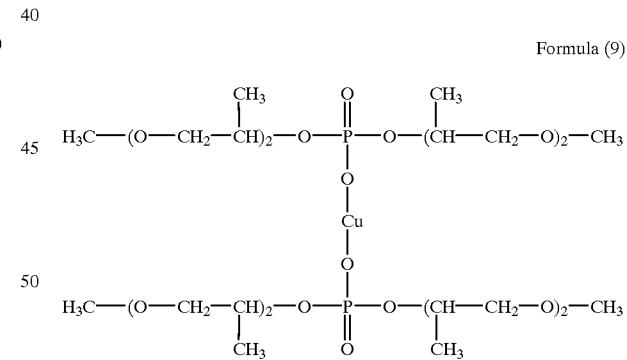

The phosphate copper compound (1 g) and Ester (n) (1.03 g) were added to methyl methacrylate (20 g), and stirring and mixing were conducted at 60° C. for 1 hour, thereby obtaining a blue and transparent monomer composition. t-Butyl peroxypivalate (0.3 g) was added to the monomer composition thus obtained, and the resultant mixture was successively heated at different temperatures of 45° C. for 16 hours, 60° C. for 8 hours and 90° C. for 3 hours to polymerize the methyl methacrylate, thereby preparing an acrylic resin composition containing the phosphate copper compound according to the present invention. The resin composition was evaluated in the same manner as in Example 6. The results are shown in Table 4.

The phosphate copper compound (1 g) and Ester (p) (1.08 g) were added to methyl methacrylate (20 g), and stirring and mixing were conducted at 60° C. for 1 hour, thereby obtaining a blue and transparent methyl methacrylate solution. The thus-obtained methyl methacrylate solution was used to conduct a process in the same manner as in Example 18, thereby preparing an acrylic resin composition containing the phosphate copper compound according to the present invention to evaluate it. The results are shown in Table 4.

EXAMPLE 20

A four-necked flask was equipped with a stirrer, a thermometer and a condenser and charged with Ester (r) (475 g;

1.0 mol) as the specific phosphate compound, toluene (480 g) as a solvent and copper acetate monohydrate (100 g; 0.5 mol). The temperature of the mixture was gradually raised, and the mixture was stirred at 40° C. for 1 hour and further at 80° C. for 3 hours, thereby reacting the specific phosphate compound with copper acetate monohydrate to obtain a blue and transparent solution. The solution was subjected to a distillation treatment to remove acetic acid formed by the reaction of the specific phosphate compound with copper acetate monohydrate and toluene, thereby obtaining a phosphate copper compound (455 g) according to the present invention. The yield was 90.0%.

Figure 9:
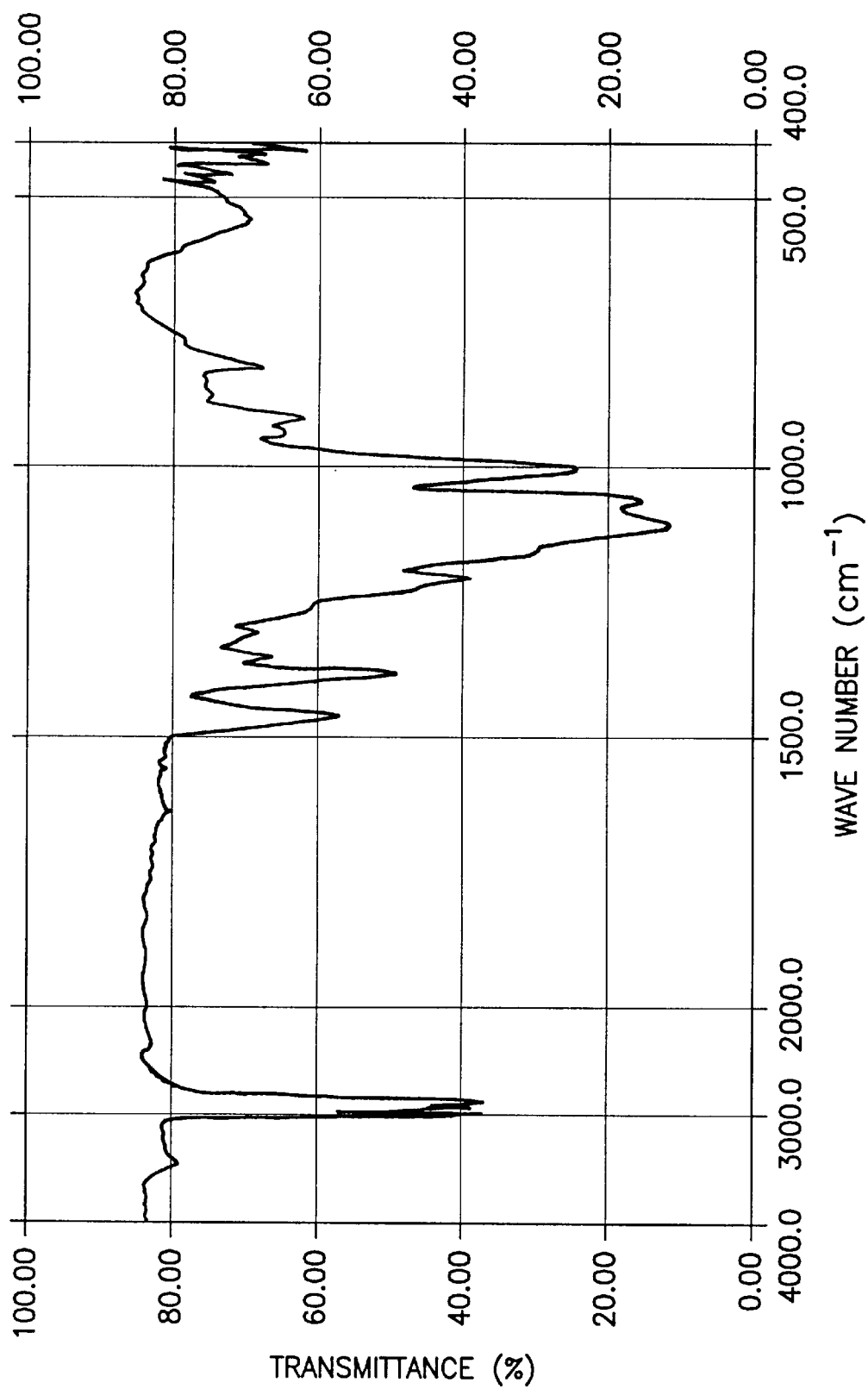
FIG. 9 diagrammatically illustrates an infrared spectral curve of a phosphate copper compound obtained in the following Example 20.

The thus-obtained phosphate copper compound had a structure represented by the following formula (10) and was in the form of a viscous liquid. The phosphate copper compound was analyzed. As a result, the content of phosphorus was 6.20% by weight (theoretical value: 6.13% by weight), and the content of copper was 6.33% by weight (theoretical value: 6.29% by weight). Incidentally, the infrared absorption curve of the phosphate copper compound thus obtained is illustrated in FIG. 9.

Formula (10)

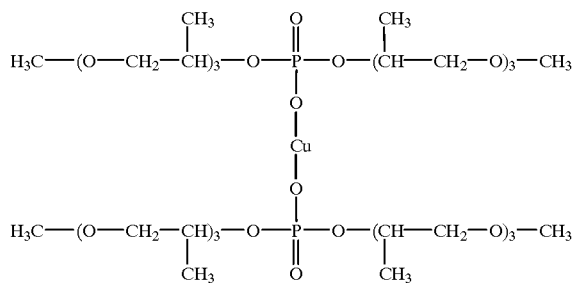

The phosphate copper compound (1 g) and Ester (r) (1.18 g) were added to methyl methacrylate (20 g), and stirring and mixing were conducted at 60° C. for 1 hour, thereby obtaining a blue and transparent methyl methacrylate solution. The thus-obtained methyl methacrylate solution was used to conduct a process in the same manner as in Example 18, thereby preparing an acrylic resin composition containing the phosphate copper compound according to the present invention to evaluate it. The results are shown in Table 4.

EXAMPLE 21

Ester (c) (0.4 g) and Ester (d) (1.6 g) as the specific phosphate compounds and anhydrous copper benzoate (1.3 g) were added to toluene (20 g), and the resultant mixture was stirred and mixed at 60° C. for 1 hour, thereby reacting the specific phosphate compounds with anhydrous copper benzoate to obtain a blue and transparent toluene solution containing the phosphate copper compounds according to the present invention.

The whole amount of the toluene solution was added to polymethyl methacrylate beads ("MHGA", product of Sumitomo Chemical Co., Ltd.; 40 g) to stir and mix them. Thereafter, the resultant mixture was dried under reduced pressure at 60° C. for 24 hours to conduct a treatment for removing toluene, thereby obtaining a massive product. The massive product was ground and then kneaded for 5 minutes by rolls heated to 180° C., thereby obtaining a blue and transparent resin composition.

The resin composition was press-molded, thereby producing a plate having a thickness of 2 mm to evaluate it in the same manner as in Example 6. The results are shown in Table 4.

TABLE 4

| | Example | | | |
|---|---|---|---|---|
| | 18 | 19 | 20 | 21 |
| Content of copper ion (% by weight) | 0.51 | 0.31 | 0.22 | 0.60 |
| Light transmittance Wavelength of 550 nm (%) | >70 | >70 | >70 | >70 |
| Wavelength of 800 nm (%) | 9 | 18 | 30 | 28 |
| Wavelength of 900 nm (%) | 17 | 18 | 35 | 35 |
| Change in light transmittance after weathering test | None | None | None | None |

As apparent from the results shown in Tables 3 and 4, it was confirmed that the resin compositions containing the respective phosphate copper compounds according to the present invention have excellent visible ray-transmitting property and performance that near infrared rays are absorbed with high efficiency, and are little in the deterioration of their near infrared ray-absorbing ability by ultraviolet rays.

EXAMPLE 22

A four-necked flask was equipped with a stirrer, a thermometer and a condenser and charged with Ester (n) (242 g; 1.0 mol) as the specific phosphate compound and toluene (250 g) as a solvent. The mixture was cooled to 5° C., and 25% aqueous sodium hydroxide (160 g, 1.0 mol as sodium hydroxide) was gradually added to the solution while keeping the temperature of the solution at 5 to 20° C., thereby neutralizing Ester (n). Thereafter, an aqueous solution with copper (II) sulfate pentahydrate (250 g; 1 mol) dissolved in water (750 g) was added to this solution over 1 hour while keeping the temperature of the solution at 20° C. The temperature of the solution was gradually raised to react Ester (n) with copper (II) sulfate under conditions of 80° C. and 5 hours. After sodium sulfate and sodium copper (II) sulfate formed in the reaction mixture were removed by filtration, the reaction mixture was left at rest, thereby separating the reaction mixture into a toluene layer and a water layer to recover the toluene solution. Toluene (200 g) was then added to the residual aqueous solution to conduct an extraction treatment of the reaction product contained in the aqueous solution, and a toluene solution was recovered. This process was conducted repeatedly 3 times, thereby recovering the toluene solution in an amount of 1020 g in total. After the condenser installed in the four-necked flask was replaced by a distiller, a treatment for removing toluene and the like from the toluene solution was conducted by this distiller, thereby obtaining a reaction product (180 g). The yield was 66.0%.

Figure 10:
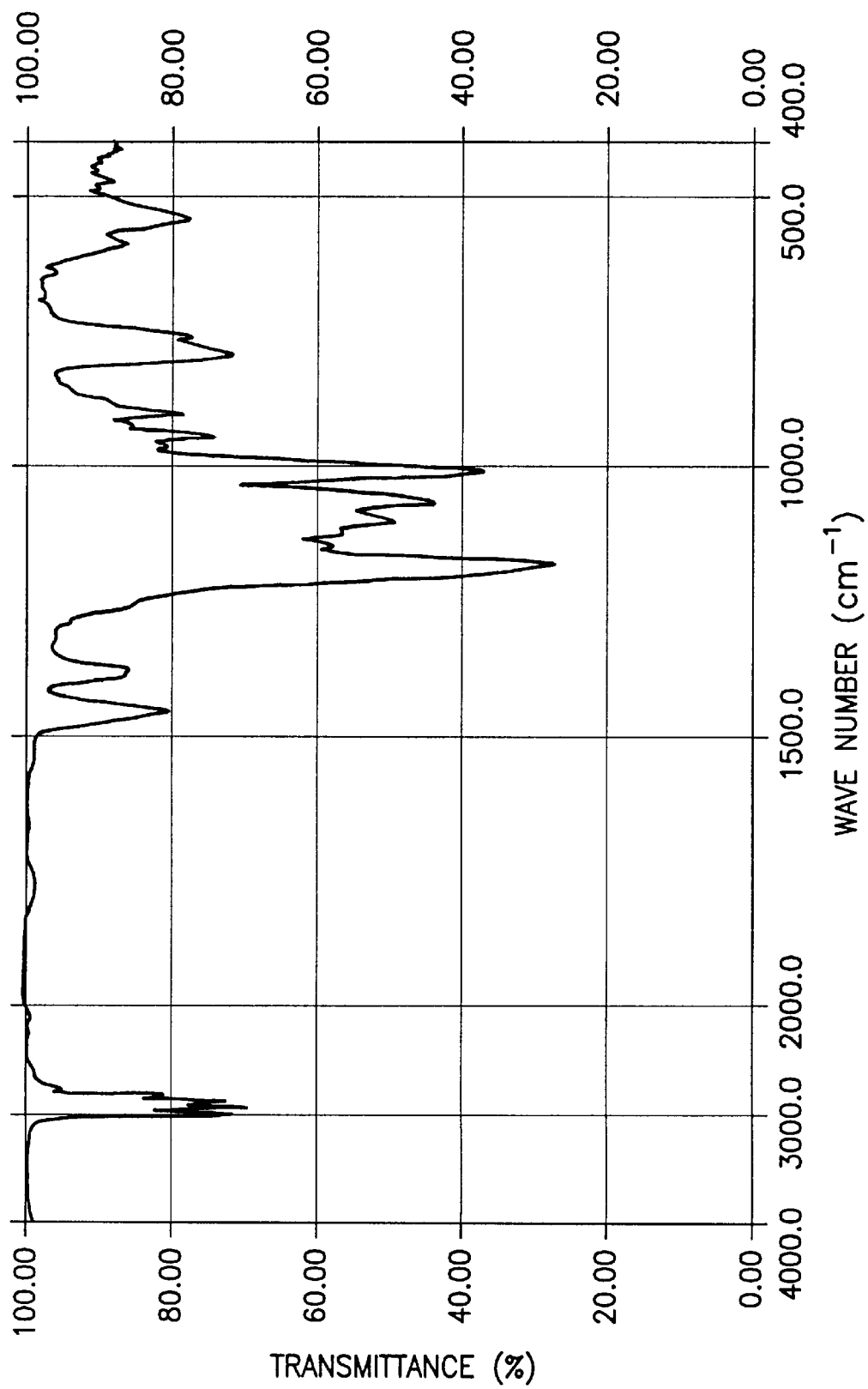
FIG. 10 diagrammatically illustrates an infrared spectral curve of a phosphate copper compound obtained in the following Example 22.

The thus-obtained phosphate copper compound had the structure represented by the above formula (8). The phosphate copper compound was analyzed. As a result, the content of phosphorus was 11.26% by weight (theoretical value: 11.35% by weight), and the content of copper was 11.04% by weight (theoretical value: 11.64% by weight). This compound had no clear melting point, and its decomposition temperature was 240° C. Incidentally, the infrared absorption curve of the phosphate copper compound thus obtained is illustrated in FIG. 10.

Effects of the Invention

According to the phosphate compounds of the present invention, a copper ion can be dispersed in a high proportion in a synthetic resin, since they have a hydroxyl group capable of being ionically or coordinately bonded to the copper ion, and are good in compatibility with synthetic resins, for example, acrylic resins. Accordingly, the phosphate compounds according to the present invention are suitable for use as additives for resins for dispersing a copper ion in synthetic resins.

According to the process of the present invention for preparing a phosphate compound, the phosphate compound can be prepared with advantages.

The phosphate copper compounds according to the present invention have performance that near infrared rays are absorbed with high efficiency, and are little in the deterioration of its near infrared ray-absorbing ability by ultraviolet rays and satisfactory in compatibility with synthetic resins, for example, acrylic resins.

According to the process of the present invention for preparing a phosphate copper compound, the phosphate copper compound can be prepared with advantages.

According to the near infrared ray absorbers of the present invention, a copper ion, which is a near infrared ray-absorbing component, can be dispersed in a high proportion in a synthetic resin because the above-mentioned phosphate compound is contained therein, and the resin compositions, to which the near infrared ray absorber according to the present invention is added, have excellent visible ray-transmitting property and performance that near infrared rays are absorbed with high efficiency and are little in the deterioration of its near infrared ray-absorbing ability by ultraviolet rays.

According to the near infrared ray absorbers of the present invention, resin compositions, which have performance that near infrared rays are absorbed with high efficiency and are little in the deterioration of its near infrared ray-absorbing ability by ultraviolet rays and excellent in visible ray-transmitting property, can be provided by containing such an absorber in a synthetic resin, since the near infrared ray absorbers comprise the phosphate copper compound as an effective ingredient.

The near infrared ray-absorbing acrylic resin compositions according to the present invention have excellent visible ray-transmitting property and performance that near infrared rays are absorbed with high efficiency and are little in the deterioration of its near infrared ray-absorbing ability by ultraviolet rays.

What is claimed is:

1. A near infrared ray-absorbing synthetic resin composition comprising a synthetic resin, and the following component (A) and/or component (B) dispersed in the synthetic resin:

Component (A): a component composed of a copper ion and a phosphate compound represented by the following formula (1); and/or Component (B): a component composed of a compound obtained by reacting a phosphate compound represented by the following formula (1) with a copper salt

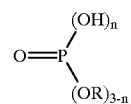

Formula (1)

wherein groups R independently mean a group represented by the following formula (2) or (3), and n is 1 or 2:

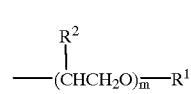

Formula (2)

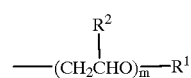

Formula (3)

wherein $R^1$ denotes an alkyl group having 1 to 20 carbon atoms, $R^2$ represents a hydrogen atom or an alkyl group having 1 to 4 carbon atoms, and m is an integer of 1 to 6.

2. The near infrared ray-absorbing synthetic resin composition according to claim 1, wherein the component (B) is composed of the phosphate copper compound represented by the following formula (6) or (7):

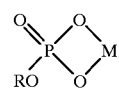

Formula (6)

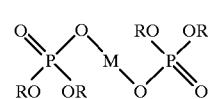

Formula (7)

wherein groups R independently mean a group represented by the following formula (2) or (3), and M denotes a copper ion:

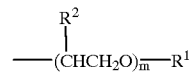

Formula (2)

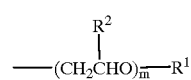

Formula (3)

wherein $R^1$ denotes an alkyl group having 1 to 20 carbon atoms, $R^2$ represents a hydrogen atom or an alkyl group having 1 to 4 carbon atoms, and m is an integer of 1 to 6.

3. The near infrared ray-absorbing synthetic resin composition according to claim 1, wherein the content of the copper ion is 0.1 to 5% by weight based on the total weight of the composition.

4. The near infrared ray-absorbing synthetic resin according to claim 1, wherein $R^2$ in the formulae (2) and (3) representing the group R in the phosphate compound represented by the formula (1), is a hydrogen atom or an alkyl group having 1 to 4 carbon atoms.

5. The near infrared ray-absorbing synthetic resin composition according to claim 1, wherein m in the formulae (2)

and (3) representing the group R in the phosphate compound represented by the formula (1), is an integer of 1 to 3.

6. The near infrared ray-absorbing synthetic resin composition according to claim 1, wherein the content of the copper ion is 0.3 to 4% by weight based on the total weight of the composition.

7. A near infrared ray-absorbing synthetic resin composition according to claim 1, wherein the content of the copper ion is 0.5 to 3% by weight based on the total weight of the composition.

8. The near infrared ray-absorbing synthetic resin composition according to claim 1, wherein the synthetic resin is acrylic resin.

9. The near infrared ray-absorbing synthetic resin composition according to claim 2, wherein the synthetic resin is acrylic resin.

10. The near infrared ray-absorbing synthetic resin composition according to claim 3, wherein the synthetic resin is acrylic resin.

11. The near infrared ray-absorbing synthetic resin composition according to claim 4, wherein the synthetic resin is acrylic resin.

12. The near infrared ray-absorbing synthetic resin composition according to claim 11, wherein m in the formulae (2) and (3) representing the group R in the phosphate compound represented by the formula (1), is an integer of 1 to 3.

* * * * *